United States Patent
Uhlmann et al.

(10) Patent No.: US 9,186,399 B2
(45) Date of Patent: Nov. 17, 2015

(54) IMMUNE STIMULATORY OLIGONUCLEOTIDE ANALOGS CONTAINING MODIFIED SUGAR MOIETIES

(75) Inventors: Eugen Uhlmann, Glashuetten (DE); Harald Debelak, Hilden (DE); Marion Jurk, Dormagen (DE); Markus Weber, Langenfeld (DE)

(73) Assignee: AdiutTide Pharmaceuticals GmbH, Frankfurt am Main (DE)

( * ) Notice: Subject to any disclaimer, the term of this patent is extended or adjusted under 35 U.S.C. 154(b) by 1394 days.

(21) Appl. No.: 12/681,800

(22) PCT Filed: Sep. 29, 2008

(86) PCT No.: PCT/IB2008/002623
§ 371 (c)(1),
(2), (4) Date: Dec. 22, 2010

(87) PCT Pub. No.: WO2009/047610
PCT Pub. Date: Apr. 16, 2009

(65) Prior Publication Data
US 2011/0098456 A1   Apr. 28, 2011

Related U.S. Application Data

(60) Provisional application No. 60/998,215, filed on Oct. 9, 2007.

(51) Int. Cl.
*A61K 39/39* (2006.01)
*A61K 39/00* (2006.01)
*C12N 15/117* (2010.01)

(52) U.S. Cl.
CPC .............. *A61K 39/39* (2013.01); *C12N 15/117* (2013.01); *A61K 2039/55561* (2013.01); *C12N 2310/17* (2013.01); *C12N 2310/32* (2013.01); *C12N 2310/322* (2013.01)

(58) Field of Classification Search
None
See application file for complete search history.

(56) References Cited

U.S. PATENT DOCUMENTS

| | | | |
|---|---|---|---|
| 4,469,863 A | 9/1984 | Ts'o et al. | |
| 5,023,243 A | 6/1991 | Tullis | |
| 5,177,198 A | 1/1993 | Spielvogel et al. | |
| 5,284,656 A | 2/1994 | Platz et al. | |
| 5,451,569 A | 9/1995 | Wong et al. | |
| 5,859,231 A | 1/1999 | Shaw et al. | |
| 6,160,109 A | 12/2000 | Just et al. | |
| 6,194,388 B1 | 2/2001 | Krieg et al. | |
| 6,207,646 B1 | 3/2001 | Krieg et al. | |
| 6,207,819 B1 | 3/2001 | Manoharan et al. | |
| 6,214,806 B1 | 4/2001 | Krieg et al. | |
| 6,218,371 B1 | 4/2001 | Krieg et al. | |
| 6,239,116 B1 | 5/2001 | Krieg et al. | |
| 6,339,068 B1 | 1/2002 | Klatt et al. | |
| 7,410,975 B2 * | 8/2008 | Lipford et al. | 514/266.2 |
| 8,188,254 B2 * | 5/2012 | Uhlmann et al. | 536/24.2 |
| 8,198,251 B2 * | 6/2012 | Vollmer et al. | 514/44 R |
| 8,283,328 B2 * | 10/2012 | Krieg et al. | 514/44 R |
| 8,304,396 B2 * | 11/2012 | Krieg et al. | 514/44 R |
| 8,349,812 B2 * | 1/2013 | Debelak et al. | 514/52 |
| 8,420,396 B2 * | 4/2013 | Uhlmann et al. | 435/455 |
| 8,580,268 B2 * | 11/2013 | Debelak et al. | 424/184.1 |
| 8,772,469 B2 * | 7/2014 | Uhlmann et al. | 536/24.5 |
| 2003/0148976 A1 | 8/2003 | Krieg et al. | |
| 2005/0239733 A1 | 10/2005 | Jurk et al. | |
| 2006/0019916 A1 | 1/2006 | Krieg et al. | |
| 2008/0045473 A1 | 2/2008 | Uhlmann et al. | |
| 2011/0098456 A1 * | 4/2011 | Uhlmann et al. | 536/23.1 |

FOREIGN PATENT DOCUMENTS

| | | | |
|---|---|---|---|
| EP | 2380584 A1 * | 10/2011 | |
| WO | WO83/01451 | 4/1983 | |
| WO | WO95/01363 | 1/1995 | |
| WO | WO00/06588 | 2/2000 | |
| WO | WO01/22990 | 4/2001 | |
| WO | WO01/62207 | 8/2001 | |
| WO | WO 2004/006941 A1 * | 1/2004 | |
| WO | WO 2007/022642 * | 3/2007 | |
| WO | WO2007/038869 | 4/2007 | |
| WO | WO2007/048244 | 5/2007 | |
| WO | WO 2007/084237 * | 7/2007 | |
| WO | WO2008/068638 | 6/2008 | |
| WO | WO 2009/047610 A1 * | 4/2009 | |

OTHER PUBLICATIONS

Abuchowski, A., et al., "Soluble Polymer-enzyme Adducts," *Enzymes as Drugs*, 1981, Chapter 13, 367-383, Hocenbberg and Roberts eds., Wiley-Interscience, New York, NY.

Adjei, A., et al., "Bioavailability of Leuprolide Following Intratracheal Administration to Beagle Dogs," *International Journal of Pharmaceutics*, 1990, vol. 61, 135-144.

Adjei, A., et al., "Pulmonary Delivery of Peptide Drugs: Effect of Particle Size on Bioavailability of Leuprolide Acetate in Healthy Male Volunteers," *Pharmaceutical Research*, 1990, vol. 7, No. 6, 565-569.

Ballas, Z., et al., "Induction of NK Activity in Murine and Human Cells by CpG Motifs in Oligodeoxynucleotides and Bacterial DNA," *The Journal of Immunology*, 1996, vol. 157, 1840-1845.

Barnes, P., et al., "Efficacy and Safety of Inhaled Corticosteroids in Asthma," *Am Rev Respir Dis*, 1993, vol. 148, S1-S26.

Braquet, P., et al., "Effect of Endothelin-1 on Blood Pressure and Bronchopulmonary System of the Guinea Pig," *Journal of Cardiovascular Pharmacology*, 1999, 13(Supplement 5), S143-S146.

Cohen, P., "CD4+T-Cells From Mice Immunized to Syngeneic Sarcomas Recognize Distinct, Non-Shared Tumor Antigens," *Cancer Research*, 1994, vol. 54, 1055-1058.

(Continued)

Primary Examiner — Nita M Minnifield
(74) Attorney, Agent, or Firm — Chalin A. Smith; Smith Patent

(57) ABSTRACT

The invention relates to oligonucleotides including at least one FANA substituted nucleotide analog and a pyrimidine-purine dinucleotide. The invention also relates to pharmaceutical compositions and methods of use thereof.

17 Claims, 4 Drawing Sheets

(56) References Cited

OTHER PUBLICATIONS

Crooke, S., et al., "Progress in Antisense Oligonucleotide Therapeutics," *Annual Review of Pharmacology and Toxicology*, 1996, vol. 6, 107-129.

Debs, R., et al., "Lung-Specific Delivery of Cytokines Induces Sustained Pulmonary and Systemic Immunomodulation in Rats," *The Journal of Immunology*, 1988, vol. 140, No. 10, 3482-3488.

Djukanovic, R., et al., "Mucosal Inflammation in Asthma," Am Rev Respir Dis, 1990, vol. 142, 434-457.

Ferrari, N., et al., "Characterization of Antisense Oligonucleotides Comprising 2'-Deoxy-2'-Fluoro-β-D-Arabinonucleic Acid (FANA), Specificity, Potency, and Duration of Activity," *Annals of The New York Academy of Science*, 2006, vol. 1082, 91-102.

Froehler, B., et al., "Triple-Helix Formation by Oligodeoxynucleotides Containing the Carbocyclic Analogs of Thymidine and 5-Methyl-2'-deoxycytidine," *Journal of the American Chemical Society*, 1992, vol. 114, 8320-8322.

Goodchild, J., "Conjugates of Oligonucleotides and Modified Oligonucleotides: A Review of Their Synthesis and Properties," *Bioconjugate Chemistry*, 1990, vol. 1, No. 3, 165-187.

Gregoriadis, G., "Liposomes for Drugs and Vaccines," *Trends in Biothechnology*, 1985, vol. 3, No. 9, 235-241.

Hacker, H., et al., "CpG-DNA-Specific Activation of Antigen-Presenting Cells Requires Stress Kinase Activity and Is Preceded by Non-Specific Endocytosis and Endosomal Maturation," *The EMBO Journal*, 1998, vol. 17, No. 21, 6230-6240.

Hartmann, G., et al., "CpG DNA: A Potent Signal for Growth, Activation, and Maturation of Human Dendritic Cells," *Proceedings of the National Academy of Science USA*, 1999, vol. 96, 9305-9310.

Hubbard, R., et al., "Anti-Neutrophil-Elastase Defenses of the Lower Respiratory Tract in α1-Antitrypsin Deficiency Directly Augmented With an Aerosol of α1-Antitrypsin," *Annals of Internal Medicine*, 1989, vol. 111, No. 3, 206-212.

Hunziker, J., et al., "Nucleic Acid Analogues: Synthesis and Properties," *Modern Synthetic Methods 1995*, 1995, vol. 7, 331-417, Weinheim, New York.

Kalota, A., et al., "2'-Deoxy-2'-Fluoro-β-D-Arabinonucleic Acid (2'F-ANA) Modified Oligonucleotides (ON) Effect Highly Efficient, and Persistent, Gene Silencing," *Nucleic Acids Research*, 2006, vol. 34, No. 2, 451-461.

Kamada, A., et al., "Issues in the Use of Inhaled Glucocorticoids," *Am J Respir Crit Care Med*, 1996, vol. 153, 1739-1748.

Krieg, a., "CpG Motifs in Bacterial DNA Trigger Direct B-Cell Activation," *Nature*, 1995, vol. 374, 546-549.

Krieg, a., "Leukocyte Stimulation by Oligodeoxynucleotides," *Applied Antisense Oligonucleotide Technology*, 1998, Chapter 24, 431-448, John Wiley & Sons, Inc., New York.

Krieg, A., "Mechanisms and Applications of Immune Stimulatory CpG Oligodeoxynucleotides," *Biochimica et Biophysica Acta*, 1999, vol. 1489, No. 1, 107-116.

Langer, R., "New Methods of Drug Delivery," *Science*, 1990, vol. 249, 1527-1533.

Liang, H., et al., "Activation of Human B Cells by Phosphorothioate Oligodeoxynucleotides," *Journal of Clinical Investigation*, 1996, vol. 98, 1119-1129.

Lipford, G., et al., "Bacterial DNA as Immune Cell Activator," *Trends in Microbiology*, 1998, vol. 6, No. 12, 496-500.

Lyer, R., et al., "3H-1, 2-Benzodithiole-3-one I,1-Dioxide as an Improved Sulfurizing Reagent in the Solid-Phase Synthesis of Oligodeoxyribonucleoside Phosphorothioates," *Journal of the American Chemical Society*, 1990, vol. 112, 1243-1254.

Matteucci, M., et al., "The Synthesis of Oligodeoxypyrimidines on a Polymer Support," *Tetrahedron Letters*, 1980, vol. 21, 719-722.

Messina, J., et al., "Stimulation of In Vitro Murine Lymphocyte Proliferation by Bacterial DNA," *The Journal of Immunology*, 1991, vol. 147, No. 6, 1759-1764.

Newmark, J., et al., "Preparation and Properties of Adducts of Streptokinase and Streptokinase-Plasmin Complex With Polyethylene Glycol and Pluronic Polyol F38," *Journal of Applied Biochemistry*, 1982, vol. 4, 185-189.

Nielsen, P., et al., "Peptide Nucleic Acid (PNA). A DNA Mimic With a Peptide Backbone," *Bioconjugate Chemistry*, 1994, vol. 5, 3-7.

Peng, C., et al., "G-Quadruplex Induced Stabilization by 2'-Deoxy-2'-Fluoro-D-Arabinonucleic Acids (2'F-ANA)," *Nucleic Acids Research*, 2007, vol. 35, No. 15, 4977-4988.

Pisetsky, D., "The Immunologic Properties of DNA," *The Journal of Immunology*, 1996, vol. 156, 421-423.

Robinson, D., et al., "Predominant $T_{H2}$-Like Bronchoalveolar T-Lymphocyte Population in Atopic Asthma," *The New England Journal of Medicine*, 1992, vol. 326, 298-304.

Sergueev, D., et al., "*H*-Phosphonate Approach for Solid-Phase Synthesis of Oligodeoxyribonucleoside Boranophosphates and Their Characterization," *Journal of the American Chemical Society*, 1998, vol. 120, 9417-9427.

Smith, R., et al., "Pulmonary Deposition and Clearance of Aerozolized Alpha-1-Proteinase Inhibitor Administered to Dogs and to Sheep," *Journal of Clinical Investigation*, 1989, vol. 84, 1145-1154.

Stirchak, E., et al., Uncharged Stereoregular Nucleic Acid Analogs: 2. Morpholino Nucleoside Oligomers With Carbamate Internucleoside Linkages, *Nucleic Acids Research*, 1989, vol. 17, No. 15, 6129-6141.

Tarkoy, M., et al., "Nucleic-Acid Analogues With Contraint Conformational Flexibility in the Sugar-Phosphate Backbone ('Bicyclo-DNA')," *Helvetica Chimica Acta*, 1993, vol. 76, 481-510.

Tokunaga, T., et al., "A Synthetic Single-Stranded DNA, Poly (dG,dC), Induces Interferon-α/β and -γ, Augments Natural Killer Activity, and Supresses Tumor Growth," *Japanese Journal of Cancer Research*, 1988, vol. 79, 682-686.

Tokunaga, T., et al., "Antitumor Activity of Deoxyribonucleic Acid Fraction From *Mycobacterium bovis* BCG. I. Isolation, Physicochemical Characterization, and Antitumore Activity," *JNCI*, 1984, vol. 72, No. 4, 955-962.

Uhlmann, E., et al., "Antisense Oligonucleotides: A New Therapeutic Principle," *Chemical Reviews*, 1990, vol. 90, No. 4, 543-581.

Uhlmann, E., et al., "Oligonucleotide Analogs Containing Dephospho-Internucleoside Linkages," *Methods in Molecular Biology*, 1993, Chapter 16, 355-389, Humana Press, Totowa, New Jersey.

Vandendriessche, F., et al., "Acyclic Oligonucleotides: Possibilities and Limitations," *Tetrahedron*, 1993, vol. 49, No. 33, 7223-7238.

Wagner, R., et al., "Potent and Selective Inhibition of Gene Expression by an Antisense Heptanucleotide," *Nature Biotechnology*, 1996, vol. 14, 840-844.

Yamamoto, S., et al, "Unique Palindromic Sequences in Synthetic Oligonucleotides Are Required to Induce Inf and Augment Inf-Mediated Natural Killer Activity," *The Journal of Immunology*, 1992, vol. 148, No. 12, 4072-4076.

Yi, A., et al., "CpG Oligodeoxyribonucleotides Rescue Mature Spleen B Cells From Spontaneous Apoptosis and Promote Cell Cycle Entry," *The Journal of Immunology*, 1998, vol. 160, 5898-5906.

Zhao, Q., et al., "Site of Chemical Modifications in CpG Containing Phosphorothioate Oligodeoxynucleotide Modulates Its Immunostimulatory Activity," *Bioorganic & Medicinal Chemistry Letters*, 1999, vol. 9, 3453-3458.

Eugen Uhlmann and Joerg Vollmer, "Recent Advances in the Development of Immunostimulatory Oligonucleotides", Current Opinion in Drug Discovery & Development (2003), vol. 6(2), pp. 204-217.

E.R. Kandimalla, et al., "Toll-like Receptor 9: Modulation of Recognition and Cytokine Induction by Novel Synthetic CpG DNAs", Biochemical Society Transactions (2003), vol. 31 (3), pp. 654-658.

Adam Judge & Ian Maclachan, "Overcoming the Innate Immune Response to Small Interfering RNA", Human Gene Therapy (2008), vol. 19, pp. 1-14.

* cited by examiner

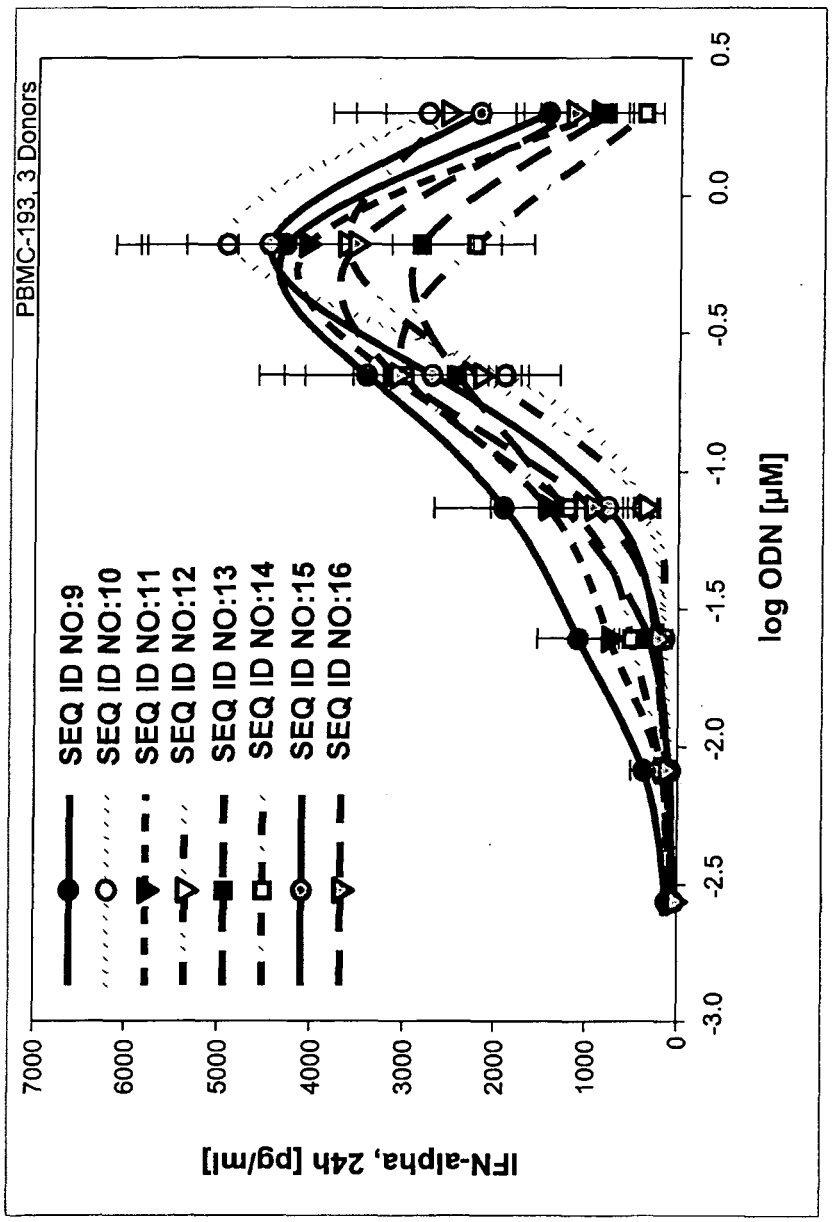

SEQUENCE LISTING

```
<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: B Class
<220> FEATURE:
<221> NAME/KEY: misc_feature
<222> LOCATION: (1)..(4)
<223> OTHER INFORMATION: Phosphorothioate Internucleotide Linkages
<220> FEATURE:
<221> NAME/KEY: modified_base
<222> LOCATION: (2)..(2)
<223> OTHER INFORMATION: FANA modified base
<220> FEATURE:
<221> NAME/KEY: misc_feature
<222> LOCATION: (5)..(20)
<223> OTHER INFORMATION: Phosphorothioate Internucleotide Linkages

<400> SEQUENCE: 1
tgtcgttttt tttttttttt                                              20

<210> SEQ ID NO 2
<211> LENGTH: 20
<212> TYPE: DNA
<213> ORGANISM: Artificial Sequence
<220> FEATURE:
```

```
<223> OTHER INFORMATION: B Class
<220> FEATURE:
<221> NAME/KEY: misc_feature
<222> LOCATION: (1)..(4)
<223> OTHER INFORMATION: Phosphorothioate Internucleotide Linkages
<220> FEATURE:
<221> NAME/KEY: modified_base
<222> LOCATION: (3)..(3)
<223> OTHER INFORMATION: FANA modified base
<220> FEATURE:
<221> NAME/KEY: misc_feature
<222> LOCATION: (5)..(20)
<223> OTHER INFORMATION: Phosphorothioate Internucleotide Linkages

<400> SEQUENCE: 2
tgtcgttttt tttttttttt                                            20

<210> SEQ ID NO 3
<211> LENGTH: 20
<212> TYPE: DNA
<213> ORGANISM: Artificial Sequence
<220> FEATURE:
<223> OTHER INFORMATION: B Class
<220> FEATURE:
<221> NAME/KEY: misc_feature
<222> LOCATION: (1)..(4)
<223> OTHER INFORMATION: Phosphorothioate Internucleotide Linkages
<220> FEATURE:
<221> NAME/KEY: modified_base
<222> LOCATION: (4)..(4)
<223> OTHER INFORMATION: FANA modified base
<220> FEATURE:
<221> NAME/KEY: misc_feature
<222> LOCATION: (5)..(20)
<223> OTHER INFORMATION: Phosphorothioate Internucleotide Linkages

<400> SEQUENCE: 3
tgtcgttttt tttttttttt                                            20

<210> SEQ ID NO 4
<211> LENGTH: 20
<212> TYPE: DNA
<213> ORGANISM: Artificial Sequence
<220> FEATURE:
<223> OTHER INFORMATION: B Class
<220> FEATURE:
<221> NAME/KEY: misc_feature
<222> LOCATION: (1)..(4)
<223> OTHER INFORMATION: Phosphorothioate Internucleotide Linkages
<220> FEATURE:
<221> NAME/KEY: misc_feature
<222> LOCATION: (5)..(20)
<223> OTHER INFORMATION: Phosphorothioate Internucleotide Linkages
<220> FEATURE:
<221> NAME/KEY: modified_base
<222> LOCATION: (5)..(5)
<223> OTHER INFORMATION: FANA modified base

<400> SEQUENCE: 4
tgtcgttttt tttttttttt                                            20

<210> SEQ ID NO 5
<211> LENGTH: 20
<212> TYPE: DNA
<213> ORGANISM: Artificial Sequence
<220> FEATURE:
<223> OTHER INFORMATION: B Class
<220> FEATURE:
<221> NAME/KEY: misc_feature
<222> LOCATION: (1)..(4)
<223> OTHER INFORMATION: Phosphorothioate Internucleotide Linkages
<220> FEATURE:
<221> NAME/KEY: modified_base
```

```
<222> LOCATION: (2)..(2)
<223> OTHER INFORMATION: FANA modified base
<220> FEATURE:
<221> NAME/KEY: misc_feature
<222> LOCATION: (5)..(20)
<223> OTHER INFORMATION: Phosphorothioate Internucleotide Linkages
<220> FEATURE:
<221> NAME/KEY: modified_base
<222> LOCATION: (5)..(5)
<223> OTHER INFORMATION: FANA modified base

<400> SEQUENCE: 5
tgtcgttttt tttttttttt                                              20

<210> SEQ ID NO 6
<211> LENGTH: 20
<212> TYPE: DNA
<213> ORGANISM: Artificial Sequence
<220> FEATURE:
<223> OTHER INFORMATION: B Class
<220> FEATURE:
<221> NAME/KEY: misc_feature
<222> LOCATION: (1)..(4)
<223> OTHER INFORMATION: Phosphorothioate Internucleotide Linkages
<220> FEATURE:
<221> NAME/KEY: misc_feature
<222> LOCATION: (5)..(20)
<223> OTHER INFORMATION: Phosphorothioate Internucleotide Linkages
<220> FEATURE:
<221> NAME/KEY: modified_base
<222> LOCATION: (6)..(6)
<223> OTHER INFORMATION: FANA modified base

<400> SEQUENCE: 6
tgtcgttttt tttttttttt                                              20

<210> SEQ ID NO 7
<211> LENGTH: 20
<212> TYPE: DNA
<213> ORGANISM: Artificial Sequence
<220> FEATURE:
<223> OTHER INFORMATION: B Class
<220> FEATURE:
<221> NAME/KEY: misc_feature
<222> LOCATION: (1)..(4)
<223> OTHER INFORMATION: Phosphorothioate Internucleotide Linkages
<220> FEATURE:
<221> NAME/KEY: misc_feature
<222> LOCATION: (5)..(20)
<223> OTHER INFORMATION: Phosphorothioate Internucleotide Linkages
<220> FEATURE:
<221> NAME/KEY: modified_base
<222> LOCATION: (7)..(7)
<223> OTHER INFORMATION: FANA modified base

<400> SEQUENCE: 7
tgtcgttttt tttttttttt                                              20

<210> SEQ ID NO 8
<211> LENGTH: 20
<212> TYPE: DNA
<213> ORGANISM: Artificial Sequence
<220> FEATURE:
<223> OTHER INFORMATION: B Class
<220> FEATURE:
<221> NAME/KEY: misc_feature
<222> LOCATION: (1)..(4)
<223> OTHER INFORMATION: Phosphorothioate Internucleotide Linkages
<220> FEATURE:
<221> NAME/KEY: misc_feature
<222> LOCATION: (5)..(20)
<223> OTHER INFORMATION: Phosphorothioate Internucleotide Linkages
```

<400> SEQUENCE: 8
tgtcgttttt tttttttttt                                          20

<210> SEQ ID NO 9
<211> LENGTH: 22
<212> TYPE: DNA
<213> ORGANISM: Artificial Sequence
<220> FEATURE:
<223> OTHER INFORMATION: C Class
<220> FEATURE:
<221> NAME/KEY: misc_feature
<222> LOCATION: (1)..(22)
<223> OTHER INFORMATION: Phosphorothioate Internucleotide Linkages
<220> FEATURE:
<221> NAME/KEY: modified_base
<222> LOCATION: (3)..(3)
<223> OTHER INFORMATION: FANA modified base

<400> SEQUENCE: 9
tcgtcgtttt cggcgcgcgc cg                                       22

<210> SEQ ID NO 10
<211> LENGTH: 22
<212> TYPE: DNA
<213> ORGANISM: Artificial Sequence
<220> FEATURE:
<223> OTHER INFORMATION: C Class
<220> FEATURE:
<221> NAME/KEY: misc_feature
<222> LOCATION: (1)..(22)
<223> OTHER INFORMATION: Phosphorothioate Internucleotide Linkages
<220> FEATURE:
<221> NAME/KEY: modified_base
<222> LOCATION: (6)..(6)
<223> OTHER INFORMATION: FANA modified base

<400> SEQUENCE: 10
tcgtcgtttt cggcgcgcgc cg                                       22

<210> SEQ ID NO 11
<211> LENGTH: 22
<212> TYPE: DNA
<213> ORGANISM: Artificial Sequence
<220> FEATURE:
<223> OTHER INFORMATION: C Class
<220> FEATURE:
<221> NAME/KEY: misc_feature
<222> LOCATION: (1)..(22)
<223> OTHER INFORMATION: Phosphorothioate Internucleotide Linkages
<220> FEATURE:
<221> NAME/KEY: modified_base
<222> LOCATION: (3)..(3)
<223> OTHER INFORMATION: FANA modified base
<220> FEATURE:
<221> NAME/KEY: modified_base
<222> LOCATION: (6)..(6)
<223> OTHER INFORMATION: FANA modified base

<400> SEQUENCE: 11
tcgtcgtttt cggcgcgcgc cg                                       22

<210> SEQ ID NO 12
<211> LENGTH: 22
<212> TYPE: DNA
<213> ORGANISM: Artificial Sequence
<220> FEATURE:
<223> OTHER INFORMATION: C Class
<220> FEATURE:
<221> NAME/KEY: misc_feature
<222> LOCATION: (1)..(22)
<223> OTHER INFORMATION: Phosphorothioate Internucleotide Linkages -continued

```
<220> FEATURE:
<221> NAME/KEY: modified_base
<222> LOCATION: (12)..(12)
<223> OTHER INFORMATION: FANA modified base
<220> FEATURE:
<221> NAME/KEY: modified_base
<222> LOCATION: (13)..(13)
<223> OTHER INFORMATION: FANA modified base
<220> FEATURE:
<221> NAME/KEY: modified_base
<222> LOCATION: (15)..(15)
<223> OTHER INFORMATION: FANA modified base
<220> FEATURE:
<221> NAME/KEY: modified_base
<222> LOCATION: (17)..(17)
<223> OTHER INFORMATION: FANA modified base
<220> FEATURE:
<221> NAME/KEY: modified_base
<222> LOCATION: (19)..(19)
<223> OTHER INFORMATION: FANA modified base

<400> SEQUENCE: 12
tcgtcgtttt cggcgcgcgc cg                                              22

<210> SEQ ID NO 13
<211> LENGTH: 22
<212> TYPE: DNA
<213> ORGANISM: Artificial Sequence
<220> FEATURE:
<223> OTHER INFORMATION: C Class
<220> FEATURE:
<221> NAME/KEY: misc_feature
<222> LOCATION: (1)..(22)
<223> OTHER INFORMATION: Phosphorothioate Internucleotide Linkages
<220> FEATURE:
<221> NAME/KEY: modified_base
<222> LOCATION: (3)..(3)
<223> OTHER INFORMATION: FANA modified base
<220> FEATURE:
<221> NAME/KEY: modified_base
<222> LOCATION: (6)..(6)
<223> OTHER INFORMATION: FANA modified base
<220> FEATURE:
<221> NAME/KEY: modified_base
<222> LOCATION: (12)..(12)
<223> OTHER INFORMATION: FANA modified base
<220> FEATURE:
<221> NAME/KEY: modified_base
<222> LOCATION: (13)..(13)
<223> OTHER INFORMATION: FANA modified base
<220> FEATURE:
<221> NAME/KEY: modified_base
<222> LOCATION: (15)..(15)
<223> OTHER INFORMATION: FANA modified base
<220> FEATURE:
<221> NAME/KEY: modified_base
<222> LOCATION: (17)..(17)
<223> OTHER INFORMATION: FANA modified base
<220> FEATURE:
<221> NAME/KEY: modified_base
<222> LOCATION: (19)..(19)
<223> OTHER INFORMATION: FANA modified base

<400> SEQUENCE: 13
tcgtcgtttt cggcgcgcgc cg                                              22

<210> SEQ ID NO 14
<211> LENGTH: 22
<212> TYPE: DNA
<213> ORGANISM: Artificial Sequence
<220> FEATURE:
<223> OTHER INFORMATION: C Class
<220> FEATURE:
<221> NAME/KEY: misc_feature
<222> LOCATION: (1)..(22)
```

```
<223> OTHER INFORMATION: Phosphorothioate Internucleotide Linkages
<220> FEATURE:
<221> NAME/KEY: modified_base
<222> LOCATION: (22)..(22)
<223> OTHER INFORMATION: 3'-O-methylguanosine
<220> FEATURE:
<221> NAME/KEY: modified_base
<222> LOCATION: (3)..(3)
<223> OTHER INFORMATION: FANA modified base
<220> FEATURE:
<221> NAME/KEY: modified_base
<222> LOCATION: (6)..(6)
<223> OTHER INFORMATION: FANA modified base
<220> FEATURE:
<221> NAME/KEY: modified_base
<222> LOCATION: (12)..(12)
<223> OTHER INFORMATION: FANA modified base
<220> FEATURE:
<221> NAME/KEY: modified_base
<222> LOCATION: (13)..(13)
<223> OTHER INFORMATION: FANA modified base
<220> FEATURE:
<221> NAME/KEY: modified_base
<222> LOCATION: (15)..(15)
<223> OTHER INFORMATION: FANA modified base
<220> FEATURE:
<221> NAME/KEY: modified_base
<222> LOCATION: (17)..(17)
<223> OTHER INFORMATION: FANA modified base
<220> FEATURE:
<221> NAME/KEY: modified_base
<222> LOCATION: (19)..(19)
<223> OTHER INFORMATION: FANA modified base

<400> SEQUENCE: 14
tcgtcgtttt cggcgcgcgc cg                                              22

<210> SEQ ID NO 15
<211> LENGTH: 22
<212> TYPE: DNA
<213> ORGANISM: Artificial Sequence
<220> FEATURE:
<223> OTHER INFORMATION: C Class
<220> FEATURE:
<221> NAME/KEY: misc_feature
<222> LOCATION: (1)..(22)
<223> OTHER INFORMATION: Phosphorothioate Internucleotide Linkages

<400> SEQUENCE: 15
tcgtcgtttt cggcgcgcgc cg                                              22

<210> SEQ ID NO 16
<211> LENGTH: 22
<212> TYPE: DNA
<213> ORGANISM: Artificial Sequence
<220> FEATURE:
<223> OTHER INFORMATION: C Class
<220> FEATURE:
<221> NAME/KEY: misc_feature
<222> LOCATION: (1)..(22)
<223> OTHER INFORMATION: Phosphorothioate Internucleotide Linkages
<220> FEATURE:
<221> NAME/KEY: modified_base
<222> LOCATION: (22)..(22)
<223> OTHER INFORMATION: 3'-O-methylguanosine

<400> SEQUENCE: 16
tcgtcgtttt cggcgcgcgc cg                                              22
```

IMMUNE STIMULATORY OLIGONUCLEOTIDE ANALOGS CONTAINING MODIFIED SUGAR MOIETIES

CROSS-REFERENCE TO RELATED APPLICATIONS

This application is a §371 filing of International Application No. PCT/IB2008/002623 filed Sep. 29, 2008, which claims the benefit of priority to U.S. Provisional Application No. 60/998,215, filed Oct. 9, 2007; the entire contents of which are incorporated herein by reference.

SEQUENCE LISTING

The instant application contains a Sequence Listing that has been submitted in ASCII format via EFS-Web and is hereby incorporated by reference in its entirety. Said ASCII copy, created on Aug. 6, 2013, is named LNK_095_ST25_08062013.txt and is 8,122 bytes in size.

BACKGROUND OF INVENTION

1. Field of Invention

The present invention relates generally to the field of immunology. More specifically the invention relates to therapeutic oligonucleotides with enhanced immunostimulatory capacity.

2. Discussion of Background Art

Bacterial DNA has immune stimulatory effects to activate B cells and natural killer cells, but vertebrate DNA does not (Tokunaga, T., et al., 1988. *Jpn. J. Cancer Res.* 79:682-686; Tokunaga, T., et al., 1984, *JNCI* 72:955-962; Messina, J. P., et al., 1991, *J. Immunol.* 147:1759-1764; and reviewed in Krieg, 1998, In: Applied Oligonucleotide Technology, C. A. Stein and A. M. Krieg, (Eds.), John Wiley and Sons, Inc., New York, N.Y., pp. 431-448). It is now understood that these immune stimulatory effects of bacterial DNA are a result of the presence of unmethylated CpG dinucleotides in particular base contexts (CpG motifs), which are common in bacterial DNA, but methylated and underrepresented in vertebrate DNA (Krieg et al, 1995 Nature 374:546-549; Krieg, 1999 Biochim. Biophys. Acta 93321:1-10). The immune stimulatory effects of bacterial DNA can be mimicked with synthetic oligodeoxynucleotides (ODN) containing these CpG motifs. Such CpG ODN have highly stimulatory effects on human and murine leukocytes, inducing B cell proliferation; cytokine and immunoglobulin secretion; natural killer (NK) cell lytic activity and IFN-γ secretion; and activation of dendritic cells (DCs) and other antigen presenting cells to express costimulatory molecules and secrete cytokines, especially the Th1-like cytokines that are important in promoting the development of Th1-like T cell responses. These immune stimulatory effects of native phosphodiester backbone CpG ODN are highly CpG specific in that the effects are dramatically reduced if the CpG motif is methylated, changed to a GpC, or otherwise eliminated or altered (Krieg et al, 1995 Nature 374:546-549; Hartmann et al, 1999 Proc. Natl. Acad. Sci USA 96:9305-10).

In early studies, it was thought that the immune stimulatory CpG motif followed the formula purine-purine-CpG-pyrimidine-pyrimidine (Krieg et al, 1995 Nature 374:546-549; Pisetsky, 1996 J. Immunol. 156:421-423; Hacker et al., 1998 EMBO J. 17:6230-6240; Lipford et al, 1998 Trends in Microbiol. 6:496-500). However, it is now clear that mouse lymphocytes respond quite well to phosphodiester CpG motifs that do not follow this "formula" (Yi et al., 1998 J. Immunol. 160:5898-5906) and the same is true of human B cells and dendritic cells (Hartmann et al, 1999 Proc. Natl. Acad. Sci USA 96:9305-10; Liang, 1996 J. Clin. Invest. 98:1119-1129).

DNA and RNA oligonucleotides are subject to digestion by exonucleases and endonucleases, which degrade internucleotide phosphate linkages at the ends of nucleic acid molecules and at internal sites, respectively. The rate of degradation can vary depending on the location of the nucleic acid, e.g., outside the cell (rapid) versus inside the cell (generally slower), as well as in the latter case the intracellular compartment containing the nucleic acid, e.g., inside the lysosome (rapid) versus in the cytoplasm (slower). Thus, increasing the stability of an oligonucleotide against nucleases has the potential to enhance its efficacy by prolonging its functional life in the cell.

A number of approaches have been reported to generate stabilized forms of RNA and DNA. See, for example, Uhlmann E et al. (1990) *Chem Rev* 90:543-84. Unfortunately, many of these approaches have not resulted in satisfactory alternatives, either because the stability gained is insufficient or because the gain in stability is associated with loss of function.

SUMMARY OF INVENTION

The present invention provides chemically modified oligonucleotides characterized by their improved stability to nucleases and acid compared to corresponding naturally occurring DNA molecules. The invention relates generally to immunomodulatory oligonucleotides that contain immunomodulatory motifs including at least one FANA modified purine nucleoside. The immunomodulatory oligonucleotides of the invention are useful in any setting or application that calls for a composition or method for modulating an immune response. The immunomodulatory oligonucleotides of the invention are of particular use in the preparation of pharmaceutical compositions, including adjuvants, vaccines, and other medicaments for use in treating a variety of conditions, including infection, cancer, allergy, autoimmune disease, inflammatory disorders, and asthma.

One aspect of the invention is an immunomodulatory oligonucleotide 8-200 nucleotides in length, comprising at least one immunomodulatory ZNYZ motif, wherein Z is a purine nucleoside or a 2'-deoxy-2'-fluoro-β-D-arabinose (FANA)-modified purine nucleoside, N is T, A, or a 5-substituted U, Y is a pyrimidine nucleoside, and wherein at least one Z comprises a FANA-modified purine nucleoside. In one embodiment the immunomodulatory motif is ZNYZ $N_1N_2N_3N_4$. In another embodiment the immunomodulatory motif is a ZNYG motif, wherein YG is an internal pyrimidine-guanine dinucleotide. In one embodiment Z is G. In another embodiment at least one G comprises a FANA-modification. In one embodiment, N is T. In another embodiment, N is 5-chloro-uracil, 5-iodo-uracil, 5-ethyl-uracil, 5-propyl-uracil, 5-propinyl-uracil, or (E)-5-(2-bromovinyl)-uracil. In one embodiment the oligonucleotide includes at least 4 nucleotides 5' to the immunomodulatory motif. In another embodiment at least one nucleotide outside of the immunomodulatory motif has a FANA modification. In one embodiment the oligonucleotide is not an antisense oligonucleotide. In another embodiment the oligonucleotide comprises a plurality of internal YZ dinucleotides. In yet another embodiment the Z of every internal YZ dinucleotide comprises a FANA-modification. In some embodiments Z is a guanosine, 2'-deoxyguanosine, 2' deoxy-7 deazaguanosine, 2' deoxy-6-thioguanosine, arabinoguanosine, 2'-deoxyinosine, 2'-deoxy 2'-substituted-arabinoguanosine, 2'-O-substituted-arabinoguanosine or other non-natural purine nucleoside. In one embodiment Z is G. In one embodiment the Y is C and Z is G, and wherein the C of the CG dinucleotide is unmethylated. In another embodiment Y is cytosine, 2'-deoxycytosine, 2'-deoxythymidine, arabinocytidine, 1-(2'-deoxy-B-D-ribofuranosyl)-2-oxo-7-deaza-8-methyl purine, 2'-deoxy-2'-substituted arabinocytidine, 2-O-substituted arabinocytidine, 2'-deoxy-5-hydroxycytidine, 2'-deoxy-N4-alkyl cytidine, 2'-deoxythiouridine or other non-natural pyrimidine nucleoside.

In one embodiment the immunomodulatory oligonucleotide is an immunostimulatory oligonucleotide. In another embodiment the immunomodulatory oligonucleotide is an immunosuppressive oligonucleotide. In various embodiments the immunomodulatory oligonucleotide is an A, B, C, P, T, E, or S class oligonucleotide.

In one embodiment the oligonucleotide is less than 15 nucleotides long. In another embodiment the oligonucleotide has at least one stabilized internucleotide linkage. In one embodiment the at least one stabilized internucleotide linkage is selected from the group consisting of: phosphorothioate, phosphorodithioate, methylphosphonate, methylphosphorothioate, phosphonoacetate, Rp-phosphorothioate, Sp-phosphorothioate, boranophosphate, or 3'-thioformacetal. In one embodiment the oligonucleotide has a second type of sugar modification. In one embodiment the second type of sugar modification is chosen from the group consisting of 2'-O-methylribose, 2'-O-propanylribose, 2'-O-butylribose, 2'-O-(2-methoxyethyl), 2'-O, 4'-C-alkylene-linked ribose (alkylene is methylene (LNA) or ethylene), 2'-deoxy-2'-fluororibose, 3'-O-methylribose, 1',2'-dideoxyribose; arabinose, 1'-methylarabinose, 3'-hydroxymethylarabinose, 4'-hydroxymethyl-arabinose, or 1,5-anhydrohexitol.

In one embodiment the oligonucleotide has at least one 3'-3' internucleotide linkage. In another embodiment the oligonucleotide has at least one 5'-5' internucleotide linkage. In yet another embodiment the oligonucleotide has at least one 2'-5' internucleotide linkage. In one embodiment the oligonucleotide is a branched oligonucleotide. In another embodiment the oligonucleotide has at least one palindromic sequence. In another embodiment the oligonucleotide has at least one $(G)_n$ sequence (n is 4 to 10). In another embodiment the oligonucleotide comprises at least one hydrophobic T analog. In another embodiment the oligonucleotide comprises at least one 5-substituted U analog. In yet another embodiment the oligonucleotide has a lipophilic modification. In one embodiment the oligonucleotide includes a linker. In another embodiment the linker is d-Spacer, 1,3-propanediol linker, glycerol or glycerol homolog.

Another aspect of the invention is a method of stimulating an immune response in a subject, comprising administering to a subject any of the immunomodulatory oligonucleotides of the invention in an effective amount to stimulate the immune response. In one embodiment, the method is a method for treating cancer in a subject, comprising administering to a subject having cancer any of the immunomodulatory oligonucleotides of the invention in an effective amount to treat the cancer. In another embodiment the method further comprises administering to the subject an anticancer treatment. In one embodiment the anti-cancer treatment is radiation therapy, chemotherapy, immunotherapy, a cancer vaccine, hormone therapy, or a biological response modifier. In one embodiment the method is a method for treating infectious disease in a subject, comprising administering to a subject having or at risk of having infectious disease any of the immunomodulatory oligonucleotides of the invention in an effective amount to treat the infectious disease. In one embodiment the immunomodulatory oligonucleotide is administered intravenously.

In another embodiment the immunomodulatory oligonucleotide is administered subcutaneously. In one embodiment the infectious disease is a viral disease. In another embodiment the viral disease is Hepatitis B, Hepatitis C, Cytomegalovirus, (CMV), Papilloma Virus, HIV or Herpes simplex viruses (HSV). In yet another embodiment the infectious disease is Leishmania, Listeria, or Anthrax. In still another embodiment the method further comprises administering to the subject an anti-viral agent, an anti-bacterial agent, an anti-parasitic agent, or an anti-fungal agent. In one embodiment the method is a method for treating allergy in a subject, comprising administering to a subject having allergy any of the immunomodulatory oligonucleotides of the invention in an effective amount to treat the allergy. In one embodiment the allergy is allergic rhinitis. In another embodiment the method further comprises administering to the subject an anti-allergy medicament. In one embodiment the subject is a subject having or at risk of having atopic dermatitis (eczema), allergic rhinitis or coryza, hay fever, conjunctivitis, bronchial asthma, urticaria (hives), or a food allergy. In another embodiment the anti-allergy medicament is an anti-IgE antibody, an antihistamine, a corticosteroid, or a prostaglandin inducer. In one embodiment the method is a method for treating asthma in a subject, comprising administering to a subject having asthma any of the immunomodulatory oligonucleotides of the invention in an effective amount to treat the asthma. In one embodiment the method further comprises administering to the subject an asthma medicament. In one embodiment the asthma medicament is a PDE-4 inhibitor, a bronchodilator/beta-2 agonist, a K+ channel opener, a VLA-4 antagonist, a neurokin antagonist, a thromboxane A2 (TXA2) synthesis inhibitor, a xanthine, an arachidonic acid antagonist, a 5 lipoxygenase inhibitor, a TXA2 receptor antagonist, a TXA2 antagonist, an inhibitor of 5-lipox activation proteins, or a protease inhibitor. In another embodiment, the method is a method of suppressing an immune response in a subject, comprising administering to a subject any of the immunomodulatory oligonucleotides of the invention in an effective amount to suppress the immune response. In another embodiment the subject has an inflammatory disorder or autoimmune disease. In another embodiment the subject is a subject having autoimmune disease. In another embodiment the subject is a subject having or at risk of having an inflammatory disorder. In yet another embodiment the inflammatory disorder is sepsis.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 4 is a graph showing that incorporation of FANA-G in the CpG motif leads to an increase of hTLR9-mediated IFN-α production. The activities of C-class FANA nucleic acids SEQ ID NO:9-14 were compared to the activity of the non-FANA parent SEQ ID NO:15 and SEQ ID NO:16 (parent with 3'-O-methylguanosine at 3' end). Human PBMC were incubated for 24 h with increasing amounts of C-class nucleic acids and IFN-α levels were determined by ELISA. Results show the mean±SEM of 3 Donors. The x-axis is log of ODN concentration in μM and the y-axis is IFN-α concentration in pg/ml.

DETAILED DESCRIPTION

Figure 1:
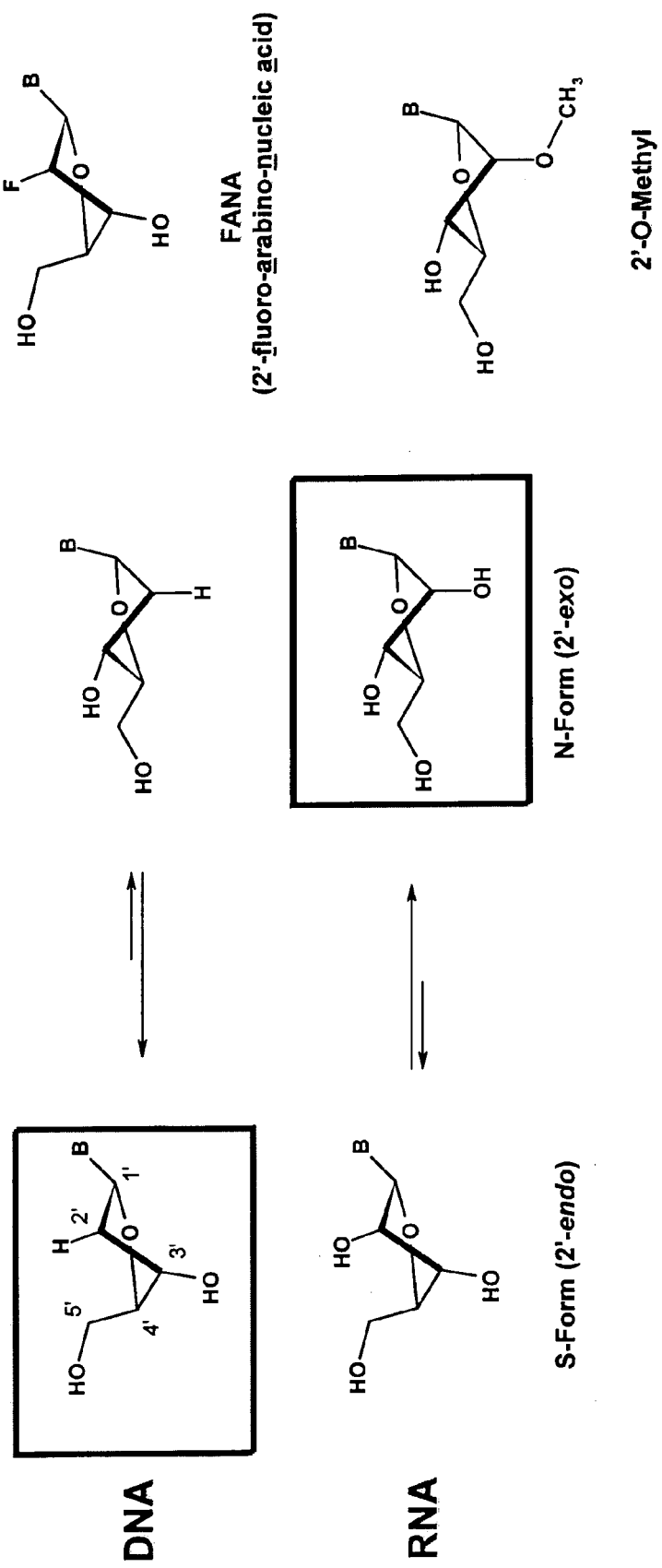
FIG. 1 is a drawing showing chemical structures for 2'-fluoro-arabino-nucleic acids (FANA) and 2'O-methyl (2'OMe). The drawing also depicts different forms of FANA and 2'OMe, demonstrating that 2'-fluoro-arabino-nucleic acids are in the preferred B-DNA conformation (2'-endo).

The invention is based in part on immunomodulatory oligonucleotides that have increased stability without a concomitant reduction in immunomodulatory capacity. Oligonucleotides (ODN) with certain immunomodulatory motifs are known to stimulate the immune system, for example through interaction with toll-like receptor 9 (TLR9). However, oligonucleotides are subject to degradation by endo- and exo-nucleases in vivo. Certain chemical modifications of CpG ODNs, such as variations of the internucleotide linkages or alteration of the sugar residue, are used to modulate their stability against nucleases, as well as their cellular uptake characteristics and their immunostimulatory profile. Unfortunately these modifications in some cases can result in a certain loss of the ability of these oligonucleotides to stimulate the immune system, presumably by interfering with the recognition of these oligonucleotides by their receptors.

The invention is related in some aspects to the discovery that replacement of 2'-deoxy-β-D-ribonucleosides in immunomodulatory oligonucleotides by inclusion of 2'-deoxy-2'-fluoro-β-D-arabino (FANA) modified nucleosides confers the desired stability on the ODN but left the biological activity intact. In addition, it was surprisingly discovered that these ODN were also more stable at acid pH, indicating potential for FANA-modified ODN in oral applications. Such increased activity was even observed when the FANA is positioned on an internal nucleoside within the stimulatory motif.

In some aspects of the invention the oligonucleotide has the immunomodulatory motif sequence ZNYZ, wherein Z is each independently a purine nucleoside or a FANA-modified purine nucleoside, N is T, A, or a 5-substituted U. Y is a pyrimidine nucleoside. In the immunomodulatory motifs of the instant invention at least one Z is a FANA-modified purine nucleoside. The oligonucleotide may include one or more such motifs. In some instances the oligonucleotide has a plurality of internal YZ dinucleotides. One or more of these dinucleotides may have a FANA-modified purine. In some instances, all of the YZ dinucleotides have a FANA-modified purine.

In some instances the immunomodulatory motif is further defined as a ZNYG motif, wherein YG is an internal pyrimidine-guanine dinucleotide. In some embodiments N is T. The immunomodulatory motif may be downstream of four or more nucleotides. The internal pyrimidine-guanine dinucleotide is typically unmethylated.

In some instances the immunomodulatory motif is further defined as ZNYZ $N_1N_2N_3N_4$, where N is either T or A.

In some instances Z is a guanosine, 2'-deoxyguanosine, 2' deoxy-7 deazaguanosine, 2' deoxy-6-thioguanosine, arabinoguanosine, 2'-deoxyinosine, 2'-deoxy 2'-substituted-arabinoguanosine, 2'-O-substituted-arabinoguanosine or other non-natural purine nucleoside.

In some instances there is more than one FANA-modified purine nucleoside in the immunomodulatory motifs described above. In some instances there are one or more FANA-modified purine nucleosides outside the motif.

The immunomodulatory oligonucleotides of the instant invention may be immunostimulatory oligonucleotides. The immunomodulatory motifs described above can be used in the context of previously described classes of immunostimulatory oligonucleotides including ODN classes such as A class, B class, C class, E class, T class and P class. In some embodiments of the invention the immunomodulatory oligonucleotides include immunostimulatory motifs which are "CpG dinucleotides". A CpG dinucleotide can be methylated or unmethylated. An immunostimulatory oligonucleotide containing at least one unmethylated CpG dinucleotide is an oligonucleotide molecule which contains an unmethylated cytosine-guanine dinucleotide sequence (i.e., an unmethylated 5' cytidine followed by 3' guanosine and linked by a phosphate bond) and which activates the immune system; such an immunostimulatory oligonucleotide is a CpG oligonucleotide. CpG oligonucleotides have been described in a number of issued patents, published patent applications, and other publications, including U.S. Pat. Nos. 6,194,388; 6,207, 646; 6,214,806; 6,218,371; 6,239,116; and 6,339,068. An immunostimulatory oligonucleotide containing at least one methylated CpG dinucleotide is an oligonucleotide which contains a methylated cytosine-guanine dinucleotide sequence (i.e., a methylated 5' cytidine followed by a 3' guanosine and linked by a phosphate bond) and which activates the immune system. In other embodiments the immunostimulatory oligonucleotides are free of CpG dinucleotides. These oligonucleotides which are free of CpG dinucleotides are referred to as non-CpG oligonucleotides, and they have non-CpG immunostimulatory motifs. Preferably these are T-rich ODN, such as ODN having at least 80% T.

"B class" ODN are potent at activating B cells but are relatively weak in inducing IFN-α and NK cell activation. The B class CpG oligonucleotides typically are fully stabilized and include an unmethylated CpG dinucleotide within certain preferred base contexts. See, e.g., U.S. Pat. Nos. 6,194,388; 6,207,646; 6,214,806; 6,218,371; 6,239,116; and 6,339,068. Another class is potent for inducing IFN-α and NK cell activation but is relatively weak at stimulating B cells; this class has been termed the "A class". The A class CpG oligonucleotides typically have stabilized poly-G sequences at 5' and 3' ends and a palindromic phosphodiester CpG dinucleotide-containing sequence of at least 6 nucleotides. See, for example, published patent application PCT/US00/26527 (WO 01/22990). Yet another class of CpG oligonucleotides activates B cells and NK cells and induces IFN-α; this class has been termed the C-class.

The "C class" immunostimulatory oligonucleotides contain at least two distinct motifs have unique and desirable stimulatory effects on cells of the immune system. Some of these ODN have both a traditional "stimulatory" CpG sequence and a "GC-rich" or "B-cell neutralizing" motif. These combination motif oligonucleotides have immune stimulating effects that fall somewhere between those effects associated with traditional "class B" CpG ODN, which are strong inducers of B cell activation and dendritic cell (DC) activation, and those effects associated with a more recently described class of immune stimulatory oligonucleotides ("class A" CpG ODN) which are strong inducers of IFN-α and natural killer (NK) cell activation but relatively poor inducers of B-cell and DC activation. Krieg A M et al. (1995) *Nature* 374:546-9; Ballas Z K et al. (1996) *J Immunol* 157: 1840-5; Yamamoto S et al. (1992) *J Immunol* 148:4072-6. While preferred class B CpG ODN often have phosphorothioate backbones and preferred class A CpG ODN have mixed or chimeric backbones, the C class of combination motif immune stimulatory oligonucleotides may have either stabilized, e.g., phosphorothioate, chimeric, or phosphodiester backbones, and in some preferred embodiments, they have semi-soft backbones. This class has been described in U.S. patent application Ser. No. 10/224,523 filed on Aug. 19, 2002, the entire contents of which is incorporated herein by reference.

The "E class" oligonucleotides have an enhanced ability to induce secretion of IFN-alpha. These ODN have a lipophilic substituted nucleotide analog 5' and/or 3' of a YGZ motif. The compound of the E class formula may be, for example, any of the following lipophilic substituted nucleotide analogs: a substituted pyrimidine, a substituted uracil, a hydrophobic T analog, a substituted toluene, a substituted imidazole or pyrazole, a substituted triazole, 5-chloro-uracil, 5-bromo-uracil, 5-iodo-uracil, 5-ethyl-uracil, 5-propyl-uracil, 5-propinyl-uracil, (E)-5-(2-bromovinyl)-uracil, or 2.4-difluoro-toluene. E class oligonucleotides are described at least in provisional patent application U.S. 60/847,811.

The "T class" oligonucleotides induce secretion of lower levels of IFN-alpha when not modified as in the ODNs of the invention and IFN-related cytokines and chemokines than B class or C class oligonucleotides, while retaining the ability to induce levels of IL-10 similar to B class oligonucleotides. T class oligonucleotides are described at least in U.S. patent application Ser. No. 11/099,683, the entire contents of which are hereby incorporated by reference.

The "P class" immunostimulatory oligonucleotides have several domains, including a 5'TLR activation domain, 2 duplex forming regions and an optional spacer and 3' tail. This class of oligonucleotides has the ability in some instances to induce much higher levels of IFN-α secretion than the C-Class. The P-Class oligonucleotides have the ability to spontaneously self-assemble into concatamers either in vitro and/or in vivo. Without being bound by any particular theory for the method of action of these molecules, one potential hypothesis is that this property endows the P-Class oligonucleotides with the ability to more highly crosslink TLR9 inside certain immune cells, inducing a distinct pattern of immune activation compared to the previously described classes of CpG oligonucleotides. Cross-linking of TLR9 receptors may induce activation of stronger IFN-α secretion through the type I IFNR feedback loop in plasmacytoid dendritic cells. P class oligonucleotides are described at least in U.S. application Ser. No. 11/706,561.

The immunomodulatory oligonucleotides of the instant invention may be immunosuppressive oligonucleotides. The immunomodulatory motifs described above can be used in the context of previously described classes of immunosuppressive oligonucleotides including ODN classes such as the "S class". Inhibitory, or S class, ODN are useful whenever it is desirable to inhibit immunostimulation. Inhibitory ODN can be used for preventing and treating septic shock, inflammation, allergy, asthma, graft rejection, graft-versus host disease (GvHD), autoimmune diseases, Th1- or Th2-mediated diseases, bacterial infections, parasitic infections, spontaneous abortions, and tumors. The inhibitory ODN can be used generally to inhibit activation of all cells expressing the relevant TLRs, and more specifically to inhibit activation of antigen-presenting cells, B cells, plasmacytoid dendritic cells (pDCs), monocytes, monocyte-derived cells, eosinophils, and neutrophils. S class ODN are further described at least in U.S. application Ser. No. 10/977,560.

The immunomodulatory oligonucleotides may have a backbone of stabilized internucleotide linkages in addition to the stabilizing FANA purine nucleotide(s) or have a chimeric backbone of stabilized and phosphodiester nucleotide linkages. A "stabilized internucleotide linkage" shall mean an internucleotide linkage that is relatively resistant to in vivo degradation (e.g., via an exo- or endo-nuclease), compared to a phosphodiester internucleotide linkage. Preferred stabilized internucleotide linkages include, without limitation, phosphorothioate, phosphorodithioate, methylphosphonate, methylphosphorothioate, phosphonoacetate, Rp-phosphorothioate, Sp-phosphorothioate, boranophosphate, or 3'-thioformacetal, or combinations thereof. Other stabilized oligonucleotides include: nonionic DNA analogs, such as alkyl- and aryl-phosphates (in which the charged phosphonate oxygen is replaced by an alkyl or aryl group), phosphodiester and alkylphosphotriesters, in which the charged oxygen moiety is alkylated. Oligonucleotides which contain diol, such as tetraethyleneglycol or hexaethyleneglycol, at either or both termini have also been shown to be substantially resistant to nuclease degradation.

For purposes of the instant invention, a chimeric backbone refers to a partially stabilized backbone, wherein at least one internucleotide linkage is phosphodiester or phosphodiester-like, and wherein at least one other internucleotide linkage is a stabilized internucleotide linkage, wherein the at least one phosphodiester or phosphodiester-like linkage and the at least one stabilized linkage are different. Since boranophosphonate linkages have been reported to be stabilized relative to phosphodiester linkages, for purposes of the chimeric nature of the backbone, boranophosphonate linkages can be classified either as phosphodiester-like or as stabilized, depending on the context. For example, a chimeric backbone according to the instant invention could in one embodiment include at least one phosphodiester (phosphodiester or phosphodiester-like) linkage and at least one boranophosphonate (stabilized) linkage. In another embodiment a chimeric backbone according to the instant invention could include boranophosphonate (phosphodiester or phosphodiester-like) and phosphorothioate (stabilized) linkages. Modified backbones such as phosphorothioates may be synthesized using automated techniques employing either phosphoramidate or H-phosphonate chemistries. Aryl- and alkyl-phosphonates can be made, e.g., as described in U.S. Pat. No. 4,469,863; and alkylphosphotriesters (in which the charged oxygen moiety is alkylated as described in U.S. Pat. No. 5,023,243 and European Patent No. 092,574) can be prepared by automated solid phase synthesis using commercially available reagents. Methods for making other DNA backbone modifications and substitutions have been described. Uhlmann E et al. (1990) *Chem Rev* 90:544; Goodchild J (1990) *Bioconjugate Chem* 1:165. Methods for preparing chimeric oligonucleotides are also known. For instance patents issued to Uhlmann et al have described such techniques.

Mixed backbone modified ODN may be synthesized using a commercially available DNA synthesizer and standard phosphoramidite chemistry. (F. E. Eckstein, "Oligonucleotides and Analogues—A Practical Approach" IRL Press, Oxford, UK, 1991, and M. D. Matteucci and M. H. Caruthers, *Tetrahedron Lett.* 21, 719 (1980)) After coupling, PS linkages are introduced by sulfurization using the Beaucage reagent (R. P. Iyer, W. Egan, J. B. Regan and S. L. Beaucage, *J. Am. Chem. Soc.* 112, 1253 (1990)) (0.075 M in acetonitrile) or phenyl acetyl disulfide (PADS) followed by capping with acetic anhydride, 2,6-lutidine in tetrahydrofurane (1:1:8; v:v:v) and N-methylimidazole (16% in tetrahydrofurane). This capping step is performed after the sulfurization reaction to minimize formation of undesired phosphodiester (PO) linkages at positions where a phosphorothioate linkage should be located. In the case of the introduction of a phosphodiester linkage, e.g. at a CpG dinucleotide, the intermediate phosphorus-III is oxidized by treatment with a solution of iodine in water/pyridine. After cleavage from the solid support and final deprotection by treatment with concentrated ammonia (15 hrs at 50° C.), the ODN are analyzed by HPLC on a Gen-Pak Fax column (Millipore-Waters) using a NaCl-gradient (e.g. buffer A: 10 mM NaH$_2$PO$_4$ in acetonitrile/water=1:4/v:v pH 6.8; buffer B: 10 mM NaH$_2$PO$_4$, 1.5 M NaCl in acetonitrile/water=1:4/v:v; 5 to 60% B in 30 minutes at 1 ml/min) or by capillary gel electrophoresis. The ODN can be purified by HPLC or by FPLC on a Source High Performance column (Amersham Pharmacia). HPLC-homogeneous fractions are combined and desalted via a C18 column or by ultrafiltration. The ODN was analyzed by MALDI-TOF mass spectrometry to confirm the calculated mass.

The oligonucleotides of the invention can also include other modifications. These include nonionic DNA analogs, such as alkyl- and aryl-phosphates (in which the charged phosphonate oxygen is replaced by an alkyl or aryl group), phosphodiester and alkylphosphotriesters, in which the charged oxygen moiety is alkylated. Oligonucleotides which contain diol, such as tetraethyleneglycol or hexaethyleneglycol, at either or both termini have also been shown to be substantially resistant to nuclease degradation.

A semi-soft oligonucleotide is an immunostimulatory oligonucleotide having a partially stabilized backbone, in which phosphodiester or phosphodiester-like internucleoside linkages occur only within at least one internal pyrimidine nucleoside-guanosine (YG) dinucleotide. Semi-soft oligonucleotides can have a number of advantages over immunostimulatory oligonucleotides with fully stabilized backbones. For instance, semi-soft oligonucleotides may possess increased immunostimulatory potency relative to corresponding fully stabilized immunostimulatory oligonucleotides.

In some embodiments the YZ dinucleotide is a YG dinucleotide, in which G is guanosine or a modified guanosine. In some embodiments the guanosine is a FANA-modified guanosine.

The immunomodulatory oligonucleotides will generally include, in addition to the phosphodiester or phosphodiester-like internucleotide linkages at preferred internal positions, 5' and 3' ends that are resistant to degradation. Such degradation-resistant ends can involve any suitable modification that results in an increased resistance against exonuclease digestion over corresponding unmodified ends. For instance, the 5' and 3' ends can be stabilized by the inclusion there of at least one phosphate modification of the backbone. In a preferred embodiment, the at least one phosphate modification of the backbone at each end is independently a phosphorothioate, phosphorodithioate, methylphosphonate, or methylphosphorothioate internucleotide linkage. In another embodiment, the degradation-resistant end includes one or more nucleotide units connected by peptide or amide linkages at the 3' end.

A phosphodiester internucleotide linkage is the type of linkage characteristic of oligonucleotides found in nature. The phosphodiester internucleotide linkage includes a phosphorus atom flanked by two bridging oxygen atoms and bound also by two additional oxygen atoms, one charged and the other uncharged. Phosphodiester internucleotide linkage is particularly preferred when it is important to reduce the tissue half-life of the oligonucleotide.

A phosphodiester-like internucleotide linkage is a phosphorus-containing bridging group that is chemically and/or diastereomerically similar to phosphodiester. Measures of similarity to phosphodiester include susceptibility to nuclease digestion and ability to activate RNAse H. Thus for example phosphodiester, but not phosphorothioate, oligonucleotides are susceptible to nuclease digestion, while both phosphodiester and phosphorothioate oligonucleotides activate RNAse H. In a preferred embodiment the phosphodiester-like internucleotide linkage is boranophosphate (or equivalently, boranophosphonate) linkage. U.S. Pat. No. 5,177,198; U.S. Pat. No. 5,859,231; U.S. Pat. No. 6,160,109; U.S. Pat. No. 6,207,819; Sergueev et al., (1998) *J Am Chem Soc* 120:9417-27. In another preferred embodiment the phosphodiester-like internucleotide linkage is diasteromerically pure Rp phosphorothioate. It is believed that diasteromerically pure Rp phosphorothioate is more susceptible to nuclease digestion and is better at activating RNAse H than mixed or diastereomerically pure Sp phosphorothioate. Stereoisomers of CpG oligonucleotides are the subject of co-pending U.S. patent application Ser. No. 09/361,575 filed Jul. 27, 1999, and published PCT application PCT/US99/17100 (WO 00/06588). It is to be noted that for purposes of the instant invention, the term phosphodiester-like internucleotide linkage specifically excludes phosphorodithioate and methylphosphonate internucleotide linkages.

The immunostimulatory oligonucleotides of the instant invention can encompass various chemical modifications and substitutions, in comparison to natural RNA and DNA, involving a phosphodiester internucleotide bridge, a β-D-ribose unit and/or a natural nucleotide base (adenine, guanine, cytosine, thymine, uracil). Examples of chemical modifications are known to the skilled person and are described, for example, in Uhlmann E et al. (1990) *Chem Rev* 90:543; "Protocols for Oligonucleotides and Analogs" Synthesis and Properties & Synthesis and Analytical Techniques, S. Agrawal, Ed, Humana Press, Totowa, USA 1993; Crooke S T et al. (1996) *Annu Rev Pharmacol Toxicol* 36:107-129; and Hunziker J et al. (1995) *Mod Synth Methods* 7:331-417. An oligonucleotide according to the invention may have one or more modifications, wherein each modification is located at a particular phosphodiester internucleotide bridge and/or at a particular β-D-ribose unit and/or at a particular natural nucleotide base position in comparison to an oligonucleotide of the same sequence which is composed of natural DNA or RNA.

For example, the invention relates to an oligonucleotide which may comprise one or more modifications and wherein each modification is independently selected from:

a) the replacement of a phosphodiester internucleotide bridge located at the 3' and/or the 5' end of a nucleotide by a modified internucleotide bridge,
b) the replacement of phosphodiester bridge located at the 3' and/or the 5' end of a nucleotide by a dephospho bridge,
c) the replacement of a sugar phosphate unit from the sugar phosphate backbone by another unit,
d) the replacement of a β-D-ribose unit by a modified sugar unit, and
e) the replacement of a natural nucleotide base by a modified nucleotide base.

More detailed examples for the chemical modification of an oligonucleotide are as follows.

A phosphodiester internucleotide bridge located at the 3' and/or the 5' end of a nucleotide can be replaced by a modified internucleotide bridge, wherein the modified internucleotide bridge is for example selected from phosphorothioate, phosphorodithioate, $NR^1R^2$-phosphoramidate, boranophosphate, α-hydroxybenzyl phosphonate, phosphate-$(C_1-C_{21})$-O-alkyl ester, phosphate-$[(C_6-C_{12})$aryl-$(C_1-C_{21})$-O-alkyl]ester, $(C_1-C_8)$alkylphosphonate and/or $(C_6-C_{12})$arylphosphonate bridges, $(C_7-C_{12})$-α-hydroxymethyl-aryl (e.g., disclosed in WO 95/01363), wherein $(C_6-C_{12})$aryl, $(C_6-C_{20})$aryl and $(C_6-C_{14})$aryl are optionally substituted by halogen, alkyl, alkoxy, nitro, cyano, and where $R^1$ and $R^2$ are, independently of each other, hydrogen, $(C_1-C_{18})$-alkyl, $(C_6-C_{20})$-aryl, $(C_8-C_{14})$-aryl-$(C_1-C_8)$-alkyl, preferably hydrogen, $(C_1-C_8)$-alkyl, preferably $(C_1-C_4)$-alkyl and/or methoxyethyl, or $R^1$ and $R^2$ form, together with the nitrogen atom carrying them, a 5-6-membered heterocyclic ring which can additionally contain a further heteroatom from the group O, S and N.

The replacement of a phosphodiester bridge located at the 3' and/or the 5' end of a nucleotide by a dephospho bridge (dephospho bridges are described, for example, in Uhlmann E and Peyman A in "Methods in Molecular Biology", Vol. 20, "Protocols for Oligonucleotides and Analogs", S. Agrawal, Ed., Humana Press, Totowa 1993, Chapter 16, pp. 355 ff), wherein a dephospho bridge is for example selected from the dephospho bridges formacetal, 3'-thioformacetal, methylhydroxylamine, oxime, methylenedimethyl-hydrazo, dimethylenesulfone and/or silyl groups.

A sugar phosphate unit (i.e., a β-D-ribose and phosphodiester internucleotide bridge together forming a sugar phosphate unit) from the sugar phosphate backbone (i.e., a sugar phosphate backbone is composed of sugar phosphate units) can be replaced by another unit, wherein the other unit is for example suitable to build up a "morpholino-derivative" oligomer (as described, for example, in Stirchak E P et al. (1989) *Nucleic Acids Res* 17:6129-41), that is, e.g., the replacement by a morpholino-derivative unit; or to build up a polyamide nucleic acid ("PNA"; as described for example, in Nielsen P E et al. (1994) *Bioconjug Chem* 5:3-7), that is, e.g., the replacement by a PNA backbone unit, e.g., by 2-aminoethylglycine.

The terms "nucleic acid" and "oligonucleotide" also encompass nucleic acids or oligonucleotides with substitutions or modifications, such as in the bases and/or sugars. For example, they include nucleic acids having backbone sugars that are covalently attached to low molecular weight organic groups other than a hydroxyl group at the 2' position and other than a phosphate group or hydroxy group at the 5' position. Thus modified nucleic acids may include a 2'-O-alkylated ribose group. In addition, modified nucleic acids may include sugars such as arabinose or 2'-fluoroarabinose instead of ribose. Thus the oligonucleotides may be heterogeneous in backbone composition thereby containing any possible combination of polymer units linked together such as peptide-nucleic acids (which have an amino acid backbone with nucleic acid bases).

Oligonucleotides also include substituted purines and pyrimidines such as C-5 propyne pyrimidine and 7-deaza-7-substituted purine modified bases. Wagner R W et al. (1996) *Nat Biotechnol* 14:840-4. Purines and pyrimidines include but are not limited to adenine, cytosine, guanine, thymine, 5-methylcytosine, 5-hydroxycytosine, 5-fluorocytosine, 2-aminopurine, 2-amino-6-chloropurine, 2,6-diaminopurine, hypoxanthine, and other naturally and non-naturally occurring nucleobases, substituted and unsubstituted aromatic moieties. Other such modifications are well known to those of skill in the art.

A modified base is any base which is chemically distinct from the naturally occurring bases typically found in DNA and RNA such as T, C, G, A, and U, but which share basic chemical structures with these naturally occurring bases. The modified nucleotide base may be, for example, selected from hypoxanthine, uracil, dihydrouracil, pseudouracil, 2-thiouracil, 4-thiouracil, 5-aminouracil, 5-$(C_1-C_6)$-alkyluracil, 5-$(C_2-C_6)$-alkenyluracil, 5-$(C_2-C_6)$-alkynyluracil, 5-(hydroxymethyl)uracil, 5-chlorouracil, 5-fluorouracil, 5-bromouracil, 5-hydroxycytosine, 5-$(C_1-C_6)$-alkylcytosine, 5-$(C_2-C_6)$-alkenylcytosine, 5-$(C_2-C_6)$-alkynylcytosine, 5-chlorocytosine, 5-fluorocytosine, 5-bromocytosine, $N^2$-dimethylguanine, 2,4-diamino-purine, 8-azapurine, a substituted 7-deazapurine, preferably 7-deaza-7-substituted and/or 7-deaza-8-substituted purine, 5-hydroxymethylcytosine, N4-alkylcytosine, e.g., N4-ethylcytosine, 5-hydroxymethylcytosine, 6-thioguanine, nitropyrrole, C5-propynylpyrimidine, and diaminopurine e.g., 2,6-diaminopurine, 5-methylcytosine, 2-aminopurine, 2-amino-6-chloropurine, hypoxanthine or other modifications of a natural nucleotide bases. This list is meant to be exemplary and is not to be interpreted to be limiting.

In addition to the FANA-modifications described above, the immunomodulatory oligonucleotides of the instant invention may have other types of sugar modifications. As with the FANA modification, a β-ribose unit or a β-D-2'-deoxyribose unit can be replaced by a modified sugar unit, wherein the modified sugar unit is for example selected from β-D-ribose, α-D-2'-deoxyribose, L-2'-deoxyribose, 2'-F-2'-deoxyribose, 2'-O—$(C_1-C_6)$alkyl-ribose, preferably 2'-O—$(C_1-C_6)$alkyl-ribose is 2'-O-methylribose, 2'-O—$(C_2-C_6)$alkenyl-ribose, 2'-[O—$(C_1-C_6)$alkyl-O—$(C_1-C_6)$alkyl]-ribose, 2'-$NH_2$-2'-deoxyribose, β-D-xylo-furanose, α-arabinofuranose, 2,4-dideoxy-β-D-erythro-hexo-pyranose, and carbocyclic (described, for example, in Froehler J (1992) *Am Chem Soc* 114:8320) and/or open-chain sugar analogs (described, for example, in Vandendriessche et al. (1993) *Tetrahedron* 49:7223) and/or bicyclosugar analogs (described, for example, in Tarkov M et al. (1993) *Helv Chim Acta* 76:481). In some embodiments the modification is 2'-O-methoxyethylribose, 2'-O-propanylribose, 2'-O-butylribose, 2'-O-(2-methoxyethyl), 2'-O, 4'-C-alkylene-linked ribose (alkylene is methylene (LNA) or ethylene), 2'-deoxy-2'-fluororibose, 3'-O-methylribose, 1',2'-dideoxyribose; arabinose, 1'-methylarabinose, 3'-hydroxymethylarabinose, 4'-hydroxymethylarabinose, or 1,5-anhydrohexitol.

In particular formulas described herein a set of modified bases is defined. For instance the letter Y is used to refer to pyrimidine and in some embodiments a nucleoside containing a cytosine or a modified cytosine. A modified cytosine as used herein is a naturally occurring or non-naturally occurring pyrimidine base analog of cytosine which can replace this base without impairing the immunostimulatory activity of the oligonucleotide. Modified cytosines include but are not limited to 5-substituted cytosines (e.g. 5-methyl-cytosine, 5-fluoro-cytosine, 5-chloro-cytosine, 5-bromo-cytosine, 5-iodo-cytosine, 5-hydroxy-cytosine, 5-hydroxymethyl-cytosine, 5-difluoromethyl-cytosine, and unsubstituted or substituted 5-alkynyl-cytosine), 6-substituted cytosines, N4-substituted cytosines (e.g. N4-ethyl-cytosine), 5-aza-cytosine, 2-mercapto-cytosine, isocytosine, pseudo-isocytosine, cytosine analogs with condensed ring systems (e.g. N,N'-propylene cytosine or phenoxazine), and uracil 5'-substituted uracil analogs such as 5-fluoro-uracil, 5-bromo-uracil, 5-bromovinyl-uracil, 4-thio-uracil, 5-hydroxy-uracil, 5-propynyl-uracil. Some of the preferred cytosines include 5-methyl-cytosine, 5-fluoro-cytosine, 5-hydroxy-cytosine, 5-hydroxymethyl-cytosine, and N4-ethyl-cytosine. In another embodiment of the invention, the cytosine base is substituted by a universal base (e.g. 3-nitropyrrole, P-base), an aromatic ring system (e.g. fluorobenzene or difluorobenzene) or a hydrogen atom (dSpacer).

The letter Z is used to refer to a purine or abasic residue, in some embodiments a guanine or a modified guanine base. A modified guanine as used herein is a naturally occurring or non-naturally occurring purine base analog of guanine which can replace this base without impairing the immunostimulatory activity of the oligonucleotide. Modified guanines include but are not limited to 7-deazaguanine, 7-deaza-7-substituted guanine (such as 7-deaza-7-(C2-C6)alkynylguanine), 7-deaza-8-substituted guanine, hypoxanthine, N2-substituted guanines (e.g. N2-methyl-guanine), 5-amino-3-methyl-3H,6H-thiazolo[4,5-d]pyrimidine-2,7-dione, 2,6-diaminopurine, 2-aminopurine, purine, indole, adenine, substituted adenines (e.g. N6-methyl-adenine, 8-oxo-adenine) 8-substituted guanine (e.g. 8-hydroxyguanine and 8-bromoguanine), and 6-thioguanine. These modified guanine bases may be FANA modified residues. In another embodiment of the invention, one of the guanine bases in the immunomodulatory motif is substituted by a universal base (e.g. 4-methyl-indole, 5-nitro-indole, and K-base), an aromatic ring system (e.g. benzimidazole or dichloro-benzimidazole, 1-methyl-1H-[1,2,4]triazole-3-carboxylic acid amide) or a hydrogen atom (dSpacer). In this embodiment the other guanine base is a FANA-modified residue.

In some embodiments the oligonucleotide comprises one or more palindromic sequences. As used herein, "palindrome" and, equivalently, "palindromic sequence" shall refer to an inverted repeat, i.e., a sequence such as ABCDEE'D'C'B'A' in which A and A', B and B', etc., are bases capable of forming the usual Watson-Crick base pairs. In some cases the palindrome is GC-rich. A GC-rich palindrome is a palindrome having a base composition of at least two-thirds G's and C's. In some embodiments the GC-rich domain is preferably 3' to the "B cell stimulatory domain". In the case of a 10-base long GC-rich palindrome, the palindrome thus contains at least 8 G's and C's. In the case of a 12-base long GC-rich palindrome, the palindrome also contains at least 8 G's and C's. In the case of a 14-mer GC-rich palindrome, at least ten bases of the palindrome are G's and C's. In some embodiments the GC-rich palindrome is made up exclusively of G's and C's. In some embodiments the oligonucleotide contains more than one palindromic sequence.

DNA is a polymer of deoxyribonucleotides joined through 3'-5' phosphodiester linkages. Units of the polymer of the invention can also be joined through 3'-5' phosphodiester linkages. However, the invention also encompasses polymers having unusual internucleotide linkages, including specifically 5'-5', 3'-3', 2'-2', 2'-3', and 2'-5' internucleotide linkages.

In one embodiment such unusual linkages are excluded from the immunostimulatory DNA motif, even though one or more of such linkages may occur elsewhere within the polymer. For polymers having free ends, inclusion of one 3'-3' internucleotide linkage can result in a polymer having two free 5' ends. Conversely, for polymers having free ends, inclusion of one 5'-5' internucleotide linkage can result in a polymer having two free 3' ends.

An immunostimulatory composition of this invention can contain two or more immunostimulatory DNA motifs which can be linked through a branching unit. The internucleotide linkages can be 3'-5', 5'-5', 3'-3', 2'-2', 2'-3', or 2'-5' linkages. Thereby, the nomenclature 2'-5' is chosen according to the carbon atom of deoxyribose. However, if unnatural sugar moieties are employed, such as ring-expanded sugar analogs (e.g., hexanose, cylohexene or pyranose) or bi- or tricyclic sugar analogs, then this nomenclature changes according to the nomenclature of the monomer. The unusual internucleotide linkage can be a phosphodiester linkage, but it can alternatively be modified as phosphorothioate or any other modified linkage as described herein. Formula I shows a general structure for branched DNA oligomers and modified oligoribonucleotide analogs of the invention via a nucleotidic branching unit. Thereby $Nu_1$, $Nu_2$, and $Nu_3$ can be linked through 3'-5', 5'-5', 3'-3', 2'-2', 2'-3', or 2'-5'-linkages. Branching of DNA oligomers can also involve the use of non-nucleotidic linkers and abasic spacers. In one embodiment, $Nu_1$, $Nu_2$, and $Nu_3$ represent identical or different immunostimulatory DNA motifs.

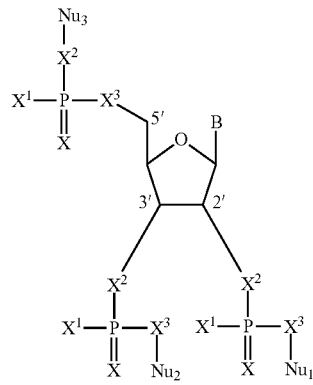

Formula I

The modified oligoribonucleotide analog may contain a doubler or trebler unit (Glen Research, Sterling, Va.), in particular those modified oligodeoxyribonucleotide analogs with a 3'-3' linkage. A doubler unit in one embodiment can be based on 1,3-bis-[5-(4,4'-dimethoxytrityloxy)pentylamido]propyl-2-[(2-cyanoethyl)-(N,N-diisopropyl)]-phosphoramidite. A trebler unit in one embodiment can be based on incorporation of Tris-2,2,2-[3-(4,4'-dimethoxytrityloxy)propyloxymethyl]ethyl-[(2-cyanoethyl)-(N,N-diisopropyl)]-phosphoramidite. Branching of the modified oligoribonucleotide analogs by multiple doubler, trebler, or other multiplier units leads to dendrimers which are a further embodiment of this invention. Branched modified oligoribonucleotide analogs may lead to crosslinking of receptors particularly for combinations of immunostimulatory RNA and DNA such as TLR3, TLR7, TLR8, and TLR9 with distinct immune effects compared to non-branched forms of the analogs. In addition, the synthesis of branched or otherwise multimeric analogs may stabilize DNA against degradation and may enable weak or partially effective DNA sequences to exert a therapeutically useful level of immune activity. The modified oligodeoxyribonucleotide analogs may also contain linker units resulting from peptide modifying reagents or oligonucleotide modifying reagents (Glen Research). Furthermore, the modified oligodeoxyribonucleotide analogs may contain one or more natural or unnatural amino acid residues which are connected to the polymer by peptide (amide) linkages.

The immunomodulatory oligonucleotide may contain at least one indirect linkage. A direct linkage refers to a phosphate or modified phosphate linkage as disclosed herein, without an intervening linker moiety. An intervening linker moiety is an organic moiety distinct from a phosphate or modified phosphate linkage as disclosed herein, which can include, for example, polyethylene glycol, 1,2-propanediol, glycerol or glycerol homolog, triethylene glycol, hexaethylene glycol, dSpacer (i.e., an abasic deoxynucleotide), doubler unit, or trebler unit.

The linkages are preferably composed of C, H, N, O, S, B, P, and Halogen, containing 3 to 300 atoms. An example with 3 atoms is an acetal linkage (ODN1-3'-O—$CH_2$—O-3'-ODN2) connecting e.g. the 3'-hydroxy group of one nucleotide to the 3'-hydroxy group of a second oligonucleotide. An example with about 300 atoms is PEG-40 (tetraconta polyethyleneglycol). Preferred linkages are phosphodiester, phosphorothioate, methylphosphonate, phosphoramidate, boranophosphonate, amide, ether, thioether, aceta, thioacetal, urea, thiourea, sulfonamide, Schiff' Base and disulfide linkages. It is also possible to use the Solulink BioConjugation System i.e., (www.trilinkbiotech.com).

If the oligonucleotide is composed of two or more sequence parts, these parts can be identical or different. Thus, in an oligonucleotide with a 3'3'-linkage, the sequences can be identical 5'-ODN1-3'3'-ODN1-5' or different 5'-ODN1-3'3'-ODN2-5'. Furthermore, the chemical modification of the various oligonucleotide parts as well as the linker connecting them may be different. Since the uptake of short oligonucleotides appears to be less efficient than that of long oligonucleotides, linking of two or more short sequences results in improved immune stimulation. The length of the short oligonucleotides is preferably 2-20 nucleotides, more preferably 3-16 nucleotides, but most preferably 5-10 nucleotides.

The oligonucleotide partial sequences may also be linked by non-nucleotidic linkers. A non-nucleotidic linker refers to any linker element that is not a nucleotide or polymer thereof (i.e., a polynucleotide), wherein a nucleotide includes a purine or pyrimidine nucleobase and a sugar phosphate, in particular abasic linkers (dSpacers), triethylene glycol units or hexaethylene glycol units. Further preferred linkers are alkylamino linkers, such as C3, C6, C12 aminolinkers, and also alkylthiol linkers, such as C3 or C6 thiol linkers. The oligonucleotides can also be linked by aromatic residues which may be further substituted by alkyl or substituted alkyl groups.

The immunomodulatory ODN of the invention may also take the form of covalently closed, dumbbell-shaped molecules with both primary and secondary structure. In one embodiment such cyclic oligoribonucleotides include two single-stranded loops connected by an intervening double-stranded segment. In one embodiment at least one single-stranded loop includes an immunomodulatory DNA motif of the invention. Other covalently closed, dumbbell-shaped molecules of the invention include chimeric DNA:RNA molecules in which, for example, the double-stranded segment is at least partially DNA (e.g., either homodimeric dsDNA or heterodimeric DNA:RNA) and at least one single-stranded loop includes an immunomodulatory DNA motif of the invention. Alternatively, the double stranded segment of the chimeric molecule is DNA.

The immunomodulatory ODN may be isolated. An isolated molecule is a molecule that is substantially pure and is free of other substances with which it is ordinarily found in nature or in in vivo systems to an extent practical and appropriate for its intended use. In particular, the immunomodulatory ODN are sufficiently pure and are sufficiently free from other biological constituents of cells so as to be useful in, for example, producing pharmaceutical preparations. Because an isolated immunomodulatory ODN of the invention may be admixed with a pharmaceutically acceptable carrier in a pharmaceutical preparation, the immunomodulatory ODN may comprise only a small percentage by weight of the preparation. The immunomodulatory ODN is nonetheless substantially pure in that it has been substantially separated from the substances with which it may be associated in living systems.

For facilitating uptake into cells, the immunostimulatory oligonucleotides are in some embodiments in the range of 8 to 100 bases in length. Typically, oligonucleotides of any size greater than 6 nucleotides (even many kb long) are capable of inducing an immune response according to the invention if sufficient immunostimulatory motifs are present. In some embodiments the oligonucleotides are at less than 15 nucleotides in length.

In one embodiment the composition of the invention further includes a polyG sequence covalently linked to at least one end of the polymer, wherein each polyG sequence independently includes 4-10 consecutive guanosine nucleosides selected from the group consisting of guanosine ribonucleoside, guanosine deoxyribonucleoside, and any combination thereof. The polyG sequence in one embodiment includes stabilized internucleotide phosphate linkages, e.g., phosphorothioate linkages. PolyG sequences can confer a number of biological and physicochemical properties, including stabilization against nucleases, enhanced uptake by cells, inhibition of certain cytokines, and formation of secondary or intermolecular structure involving so-called G-tetrads. In one embodiment the polymer has a 3' end and the polyG sequence is covalently linked to the 3' end. The polyG sequence can be covalently linked to the polymer via any suitable direct or indirect linkage, usually via a backbone linkage.

In one aspect the invention provides a conjugate of an immunomodulatory oligonucleotide of the invention and a lipophilic modification. The lipophilic group in general can be a cholesteryl, a modified cholesteryl, a cholesterol derivative, a reduced cholesterol, a substituted cholesterol, cholestan, C16 alkyl chain, a bile acid, cholic acid, taurocholic acid, deoxycholate, oleyl litocholic acid, oleoyl cholenic acid, a glycolipid, a phospholipid, a sphingolipid, an isoprenoid, such as steroids, vitamins, such as vitamin E, saturated fatty acids, unsaturated fatty acids, fatty acid esters, such as triglycerides, pyrenes, porphyrines, Texaphyrine, adamantane, acridines, biotin, coumarin, fluorescein, rhodamine, Texas-Red, digoxygenin, dimethoxytrityl, t-butyldimethylsilyl, t-butyldiphenylsilyl, cyanine dyes (e.g. Cy3 or Cy5), Hoechst 33258 dye, psoralen, or ibuprofen. In certain embodiments the lipophilic moiety is chosen from cholesteryl, palmityl, and fatty acyl. In one embodiment the lipohilic moiety is cholesteryl. It is believed that inclusion of one or more of such lipophilic moieties in the immunomodulatory oligonucleotide of the invention confers upon them yet additional stability against degradation by nucleases. Where there are two or more lipophilic moieties in a single immunomodulatory oligonucleotide of the invention, each lipophilic moiety can be selected independently of any other.

In one embodiment the lipophilic group is attached to a 2'-position of a nucleotide of the immunomodulatory oligonucleotide. A lipophilic group can alternatively or in addition be linked to the heterocyclic nucleobase of a nucleotide of the immunomodulatory oligonucleotide. The lipophilic moiety can be covalently linked to the immunomodulatory oligonucleotide via any suitable direct or indirect linkage. In one embodiment the linkage is direct and is an ester or an amide. In one embodiment the linkage is indirect and includes a spacer moiety, for example one or more abasic nucleotide residues, oligoethyleneglycol, such as triethyleneglycol (spacer 9) or hexaethyleneglycol (spacer 18), or an alkanediol, such as butanediol.

The invention encompasses the use of the immunomodulatory oligonucleotides of the instant invention for treatment of a subject having a condition that may be treated by stimulation or suppression of the immune response. Thus, the immunostimulatory oligonucleotides of the invention are useful for the treatment of infection, cancer, allergy, asthma, an inflammatory condition, or an autoimmune disease.

The immunomodulatory oligonucleotides are also useful in some aspects of the invention for the treatment of a subject at risk of developing allergy or asthma, an infection with an infectious organism, or cancer. A subject at risk as used herein is a subject who has any risk of exposure to an infection causing pathogen or a cancer or an allergen or a risk of developing cancer. For instance, a subject at risk may be a subject who is planning to travel to an area where a particular type of infectious agent is found or it may be a subject who through lifestyle or medical procedures is exposed to bodily fluids which may contain infectious organisms or directly to the organism or even any subject living in an area where an infectious organism or an allergen has been identified. Subjects at risk of developing infection also include general populations to which a medical agency recommends vaccination with a particular infectious organism antigen. If the antigen is an allergen and the subject develops allergic responses to that particular antigen and the subject may be exposed to the antigen, i.e., during pollen season, then that subject is at risk of exposure to the antigen. A subject at risk of developing allergy or asthma includes those subjects that have been identified as having an allergy or asthma but that don't have the active disease during the immunomodulatory oligonucleotide treatment as well as subjects that are considered to be at risk of developing these diseases because of genetic or environmental factors.

A subject at risk of developing a cancer is one who has a high probability of developing cancer. These subjects include, for instance, subjects having a genetic abnormality, the presence of which has been demonstrated to have a correlative relation to a higher likelihood of developing a cancer and subjects exposed to cancer causing agents such as tobacco, asbestos, or other chemical toxins, or a subject who has previously been treated for cancer and is in apparent remission. When a subject at risk of developing a cancer is treated with an antigen specific for the type of cancer to which the subject is at risk of developing and a CpG immunostimulatory oligonucleotide, the subject may be able to kill the cancer cells as they develop. If a tumor begins to form in the subject, the subject will develop a specific immune response against the tumor antigen.

A subject having an allergy is a subject that has or is at risk of developing an allergic reaction in response to an allergen. An allergy refers to acquired hypersensitivity to a substance (allergen). Allergic conditions include but are not limited to eczema, allergic rhinitis or coryza, hay fever, conjunctivitis, bronchial asthma, urticaria (hives) and food allergies, and other atopic conditions.

Allergies are generally caused by IgE antibody generation against harmless allergens. The cytokines that are induced by systemic or mucosal administration of immunomodulatory oligonucleotides are predominantly of a class called Th1 (examples are IL-12, IP-10, IFN-α and IFN-γ) and these induce both humoral and cellular immune responses. The other major type of immune response, which is associated with the production of IL-4 and IL-5 cytokines, is termed a Th2 immune response. In general, it appears that allergic diseases are mediated by Th2 type immune responses. Based on the ability of the immunomodulatory oligonucleotide to shift the immune response in a subject from a predominant Th2 (which is associated with production of IgE antibodies and allergy) to a balanced Th2/Th1 response (which is protective against allergic reactions), an effective dose for inducing an immune response of a immunomodulatory oligonucleotide can be administered to a subject to treat or prevent asthma and allergy.

Thus, the immunomodulatory oligonucleotides have significant therapeutic utility in the treatment of allergic and non-allergic conditions such as asthma. Th2 cytokines, especially IL-4 and IL-5 are elevated in the airways of asthmatic subjects. These cytokines promote important aspects of the asthmatic inflammatory response, including IgE isotype switching, eosinophil chemotaxis and activation and mast cell growth. Th1 cytokines, especially IFN-γ and IL-12, can suppress the formation of Th2 clones and production of Th2 cytokines. Asthma refers to a disorder of the respiratory system characterized by inflammation, narrowing of the airways and increased reactivity of the airways to inhaled agents. Asthma is frequently, although not exclusively associated with atopic or allergic symptoms.

The immunomodulatory oligonucleotides of the invention may also be administered in conjunction with an anti-allergy therapy. Conventional methods for treating or preventing allergy have involved the use of allergy medicaments or desensitization therapies. Some evolving therapies for treating or preventing allergy include the use of neutralizing anti-IgE antibodies. Anti-histamines and other drugs which block the effects of chemical mediators of the allergic reaction help to regulate the severity of the allergic symptoms but do not prevent the allergic reaction and have no effect on subsequent allergic responses. Desensitization therapies are performed by giving small doses of an allergen, usually by injection under the skin, in order to induce an IgG-type response against the allergen. The presence of IgG antibody helps to neutralize the production of mediators resulting from the induction of IgE antibodies, it is believed. Initially, the subject is treated with a very low dose of the allergen to avoid inducing a severe reaction and the dose is slowly increased. This type of therapy is dangerous because the subject is actually administered the compounds which cause the allergic response and severe allergic reactions can result.

Anti-allergy medicaments include, but are not limited to, anti-histamines, corticosteroids, and prostaglandin inducers. Anti-histamines are compounds which counteract histamine released by mast cells or basophils. These compounds are well known in the art and commonly used for the treatment of allergy. Anti-histamines include, but are not limited to, acrivastine, astemizole, azatadine, azelastine, betatastine, brompheniramine, buclizine, cetirizine, cetirizine analogues, chlorpheniramine, clemastine, CS 560, cyproheptadine, desloratadine, dexchlorpheniramine, ebastine, epinastine, fexofenadine, HSR 609, hydroxyzine, levocabastine, loratidine, methscopolamine, mizolastine, norastemizole, phenindamine, promethazine, pyrilamine, terfenadine, and tranilast.

Corticosteroids include, but are not limited to, methylprednisolone, prednisolone, prednisone, beclomethasone, budesonide, dexamethasone, flunisolide, fluticasone propionate, and triamcinolone. Although dexamethasone is a corticosteroid having anti-inflammatory action, it is not regularly used for the treatment of allergy or asthma in an inhaled form because it is highly absorbed and it has long-term suppressive side effects at an effective dose. Dexamethasone, however, can be used according to the invention for treating allergy or asthma because when administered in combination with a composition of the invention it can be administered at a low dose to reduce the side effects. Some of the side effects associated with corticosteroid use include cough, dysphonia, oral thrush (candidiasis), and in higher doses, systemic effects, such as adrenal suppression, glucose intolerance, osteoporosis, aseptic necrosis of bone, cataract formation, growth suppression, hypertension, muscle weakness, skin thinning, and easy bruising. Barnes & Peterson (1993) *Am Rev Respir Dis* 148:S1-S26; and Kamada A K et al. (1996) *Am J Respir Crit Care Med* 153:1739-48.

The oligonucleotides and methods of the invention can be used alone or in conjunction with other agents and methods useful for the treatment of asthma. In one aspect the invention provides a method of treating a subject having asthma. The method according to this aspect of the invention includes the step of administering to a subject having asthma an effective amount of a composition of the invention to treat the subject.

In one aspect the invention provides a method of treating a subject having asthma. The method according to this aspect of the invention includes the step of administering to a subject having asthma an effective amount of the composition of the invention and an anti-asthma therapy to treat the subject.

"Asthma" as used herein refers to a disorder of the respiratory system characterized by inflammation and narrowing of the airways, and increased reactivity of the airways to inhaled agents. Asthma is frequently, although not exclusively, associated with an atopic or allergic condition. Symptoms of asthma include recurrent episodes of wheezing, breathlessness, chest tightness, and coughing, resulting from airflow obstruction. Airway inflammation associated with asthma can be detected through observation of a number of physiological changes, such as, denudation of airway epithelium, collagen deposition beneath basement membrane, edema, mast cell activation, inflammatory cell infiltration, including neutrophils, eosinophils, and lymphocytes. As a result of the airway inflammation, asthma patients often experience airway hyper-responsiveness, airflow limitation, respiratory symptoms, and disease chronicity. Airflow limitations include acute bronchoconstriction, airway edema, mucous plug formation, and airway remodeling, features which often lead to bronchial obstruction. In some cases of asthma, sub-basement membrane fibrosis may occur, leading to persistent abnormalities in lung function.

Research over the past several years has revealed that asthma likely results from complex interactions among inflammatory cells, mediators, and other cells and tissues resident in the airways. Mast cells, eosinophils, epithelial cells, macrophage, and activated T cells all play an important role in the inflammatory process associated with asthma. Djukanovic R et al. (1990) *Am Rev Respir Dis* 142:434-457. It is believed that these cells can influence airway function through secretion of preformed and newly synthesized mediators which can act directly or indirectly on the local tissue. It has also been recognized that subpopulations of T lymphocytes (Th2) play an important role in regulating allergic inflammation in the airway by releasing selective cytokines and establishing disease chronicity. Robinson D S et al. (1992) *N Engl J Med* 326:298-304.

Asthma is a complex disorder which arises at different stages in development and can be classified based on the degree of symptoms as acute, subacute, or chronic. An acute inflammatory response is associated with an early recruitment of cells into the airway. The subacute inflammatory response involves the recruitment of cells as well as the activation of resident cells causing a more persistent pattern of inflammation. Chronic inflammatory response is characterized by a persistent level of cell damage and an ongoing repair process, which may result in permanent abnormalities in the airway.

A "subject having asthma" is a subject that has a disorder of the respiratory system characterized by inflammation and narrowing of the airways and increased reactivity of the airways to inhaled agents. Factors associated with initiation of asthma include, but are not limited to, allergens, cold temperature, exercise, viral infections, and $SO_2$.

As mentioned above, asthma may be associated with a Th2-type of immune response, which is characterized at least in part by Th2 cytokines IL-4 and IL-5, as well as antibody isotype switching to IgE. Th1 and Th2 immune responses are mutually counter-regulatory, so that skewing of the immune response toward a Th1-type of immune response can prevent or ameliorate a Th2-type of immune response, including allergy. The immunomodulatory oligonucleotides of the invention are therefore useful by themselves to treat a subject having asthma because the analogs can skew the immune response toward a Th1-type of immune response. Alternatively or in addition, the modified oligoribonucleotide analogs of the invention can be used in combination with an allergen to treat a subject having asthma.

The immunomodulatory oligonucleotides of the invention may also be administered in conjunction with an asthma therapy. Conventional methods for treating or preventing asthma have involved the use of anti-allergy therapies (described above) and a number of other agents, including inhaled agents.

Medications for the treatment of asthma are generally separated into two categories, quick-relief medications and long-term control medications. Asthma patients take the long-term control medications on a daily basis to achieve and maintain control of persistent asthma. Long-term control medications include anti-inflammatory agents such as corticosteroids, chromolyn sodium and nedocromil; long-acting bronchodilators, such as long-acting $\beta_2$-agonists and methylxanthines; and leukotriene modifiers. The quick-relief medications include short-acting $\beta_2$ agonists, anti-cholinergics, and systemic corticosteroids. There are many side effects associated with each of these drugs and none of the drugs alone or in combination is capable of preventing or completely treating asthma.

Anti-asthma medicaments include, but are not limited to, PDE-4 inhibitors, bronchodilator/beta-2 agonists, K+ channel openers, VLA-4 antagonists, neurokin antagonists, thromboxane A2 (TXA2) synthesis inhibitors, xanthines, arachidonic acid antagonists, 5 lipoxygenase inhibitors, TXA2 receptor antagonists, TXA2 antagonists, inhibitor of 5-lipox activation proteins, and protease inhibitors.

Bronchodilator/$\beta_2$ agonists are a class of compounds which cause bronchodilation or smooth muscle relaxation. Bronchodilator/$\beta_2$ agonists include, but are not limited to, salmeterol, salbutamol, albuterol, terbutaline, D2522/formoterol, fenoterol, bitolterol, pirbuerol methylxanthines and orciprenaline. Long-acting $\beta_2$ agonists and bronchodilators are compounds which are used for long-term prevention of symptoms in addition to the anti-inflammatory therapies. Long-acting $\beta_2$ agonists include, but are not limited to, salmeterol and albuterol. These compounds are usually used in combination with corticosteroids and generally are not used without any inflammatory therapy. They have been associated with side effects such as tachycardia, skeletal muscle tremor, hypokalemia, and prolongation of QTc interval in overdose.

Methylxanthines, including for instance theophylline, have been used for long-term control and prevention of symptoms. These compounds cause bronchodilation resulting from phosphodiesterase inhibition and likely adenosine antagonism. Dose-related acute toxicities are a particular problem with these types of compounds. As a result, routine serum concentration must be monitored in order to account for the toxicity and narrow therapeutic range arising from individual differences in metabolic clearance. Side effects include tachycardia, tachyarrhythmias, nausea and vomiting, central nervous system stimulation, headache, seizures, hematemesis, hyperglycemia and hypokalemia. Short-acting $\beta_2$ agonists include, but are not limited to, albuterol, bitolterol, pirbuterol, and terbutaline. Some of the adverse effects associated with the administration of short-acting $\beta_2$ agonists include tachycardia, skeletal muscle tremor, hypokalemia, increased lactic acid, headache, and hyperglycemia.

Chromolyn sodium and nedocromil are used as long-term control medications for preventing primarily asthma symptoms arising from exercise or allergic symptoms arising from allergens. These compounds are believed to block early and late reactions to allergens by interfering with chloride channel function. They also stabilize mast cell membranes and inhibit activation and release of mediators from inosineophils and epithelial cells. A four to six week period of administration is generally required to achieve a maximum benefit.

Anticholinergics are generally used for the relief of acute bronchospasm. These compounds are believed to function by competitive inhibition of muscarinic cholinergic receptors. Anticholinergics include, but are not limited to, ipratropium bromide. These compounds reverse only cholinerigically-mediated bronchospasm and do not modify any reaction to antigen. Side effects include drying of the mouth and respiratory secretions, increased wheezing in some individuals, and blurred vision if sprayed in the eyes.

The immunomodulatory oligonucleotides of the invention may also be useful for treating airway remodeling. Airway remodeling results from smooth muscle cell proliferation and/or submucosal thickening in the airways, and ultimately causes narrowing of the airways leading to restricted airflow. The immunomodulatory oligonucleotides of the invention may prevent further remodeling and possibly even reduce tissue build-up resulting from the remodeling process.

The immunomodulatory oligonucleotides of the invention may also be useful for treating cancer. A subject having a cancer is a subject that has detectable cancerous cells. The cancer may be a malignant or non-malignant cancer. Cancers or tumors include but are not limited to biliary tract cancer; brain cancer; breast cancer; cervical cancer; choriocarcinoma; colon cancer; endometrial cancer; esophageal cancer; gastric cancer; intraepithelial neoplasms; lymphomas; liver cancer; lung cancer (e.g. small cell and non-small cell); melanoma; neuroblastomas; oral cancer; ovarian cancer; pancreas cancer; prostate cancer; rectal cancer; sarcomas; skin cancer; testicular cancer; thyroid cancer; and renal cancer, as well as other carcinomas and sarcomas. In one embodiment the cancer is hairy cell leukemia, chronic myelogenous leukemia, cutaneous T-cell leukemia, multiple myeloma, follicular lymphoma, malignant melanoma, squamous cell carcinoma, renal cell carcinoma, prostate carcinoma, bladder cell carcinoma, or colon carcinoma.

The immunomodulatory oligonucleotides may be administered alone or in conjunction with an anti-cancer therapy. Anti-cancer therapies include but are not limited to radiation therapy, chemotherapy, immunotherapy, a cancer vaccine, hormone therapy, a biological response modifier, and surgical procedures. A cancer medicament refers to an agent which is administered to a subject for the purpose of treating a cancer. As used herein, "treating cancer" includes preventing the development of a cancer, reducing the symptoms of cancer, and/or inhibiting the growth of an established cancer. In other aspects, the cancer medicament is administered to a subject at risk of developing a cancer for the purpose of reducing the risk of developing the cancer. Various types of medicaments for the treatment of cancer are described herein. For the purpose of this specification, cancer medicaments are classified as chemotherapeutic agents, immunotherapeutic agents, cancer vaccines, hormone therapy, and biological response modifiers.

Additionally, the methods of the invention are intended to embrace the use of more than one cancer medicament along with the immunomodulatory oligonucleotides. As an example, where appropriate, the immunomodulatory oligonucleotides may be administered with both a chemotherapeutic agent and an immunotherapeutic agent. Alternatively, the cancer medicament may embrace an immunotherapeutic agent and a cancer vaccine, or a chemotherapeutic agent and a cancer vaccine, or a chemotherapeutic agent, an immunotherapeutic agent and a cancer vaccine all administered to one subject for the purpose of treating a subject having a cancer or at risk of developing a cancer.

The chemotherapeutic agent may be selected from the group consisting of methotrexate, vincristine, adriamycin, cisplatin, non-sugar containing chloroethylnitrosoureas, 5-fluorouracil, mitomycin C, bleomycin, doxorubicin, dacarbazine, taxol, fragyline, Meglamine GLA, valrubicin, carmustaine and poliferposan, MMI270, BAY 12-9566, RAS famesyl transferase inhibitor, famesyl transferase inhibitor, MMP, MTA/LY231514, LY264618/Lometexol, Glamolec, CI-994, TNP-470, Hycamtin/Topotecan, PKC412, Valspodar/PSC833, Novantrone/Mitroxantrone, Metaret/Suramin, Batimastat, E7070, BCH-4556, CS-682, 9-AC, AG3340, AG3433, Incel/VX-710, VX-853, ZD0101, ISI641, ODN 698, TA 2516/Marmistat, BB2516/Marmistat, CDP 845, D2163, PD183805, DX8951f, Lemonal DP 2202, FK 317, Picibanil/OK-432, AD 32/Valrubicin, Metastron/strontium derivative, Temodal/Temozolomide, Evacet/liposomal doxorubicin, Yewtaxan/Paclitaxel, Taxol/Paclitaxel, Xeload/Capecitabine, Furtulon/Doxifluridine, Cyclopax/oral paclitaxel, Oral Taxoid, SPU-077/Cisplatin, HMR 1275/Flavopiridol, CP-358 (774)/EGFR, CP-609 (754)/RAS oncogene inhibitor, BMS-182751/oral platinum, UFT (Tegafur/Uracil), Ergamisol/Levamisole, Eniluracil/776C85/5FU enhancer, Campto/Levamisole, Camptosar/Irinotecan, Tumodex/Ralitrexed, Leustatin/Cladribine, Paxex/Paclitaxel, Doxil/liposomal doxorubicin, Caelyx/liposomal doxorubicin, Fludara/Fludarabine, Pharmarubicin/Epirubicin, DepoCyt, ZD1839, LU 79553/Bis-Naphtalimide, LU 103793/Dolastain, Caetyx/liposomal doxorubicin, Gemzar/Gemcitabine, ZD 0473/Anormed, YM 116, Iodine seeds, CDK4 and CDK2 inhibitors, PARP inhibitors, D4809/Dexifosamide, Ifes/Mesnex/Ifosamide, Vumon/Teniposide, Paraplatin/Carboplatin, Plantinol/cisplatin, Vepeside/Etoposide, ZD 9331, Taxotere/Docetaxel, prodrug of guanine arabinoside, Taxane Analog, nitrosoureas, alkylating agents such as melphelan and cyclophosphamide, Aminoglutethimide, Asparaginase, Busulfan, Carboplatin, Chlorombucil, Cytarabine HCl, Dactinomycin, Daunorubicin HCl, Estramustine phosphate sodium, Etoposide (VP16-213), Floxuridine, Fluorouracil (5-FU), Flutamide, Hydroxyurea (hydroxycarbamide), Ifosfamide, Interferon Alfa-2a, Alfa-2b, Leuprolide acetate (LHRH-releasing factor analogue), Lomustine (CCNU), Mechlorethamine HCl (nitrogen mustard), Mercaptopurine, Mesna, Mitotane (o.p'-DDD), Mitoxantrone HCl, Octreotide, Plicamycin, Procarbazine HCl, Streptozocin, Tamoxifen citrate, Thioguanine, Thiotepa, Vinblastine sulfate, Amsacrine (m-AMSA), Azacitidine, Erthropoietin, Hexamethylmelamine (HMM), Interleukin 2, Mitoguazone (methyl-GAG; methyl glyoxal bis-guanylhydrazone; MGBG), Pentostatin (2'deoxycoformycin), Semustine (methyl-CCNU), Teniposide (VM-26) and Vindesine sulfate, but it is not so limited.

The immunotherapeutic agent may be selected from the group consisting of Ributaxin, Herceptin, Quadramet, Panorex, IDEC-Y2B8, BEC2, C225, Oncolym, SMART M195, ATRAGEN, Ovarex, Bexxar, LDP-03, ior t6, MDX-210, MDX-11, MDX-22, OV103, 3622W94, anti-VEGF, Zenapax, MDX-220, MDX-447, MELIMMUNE-2, MELIMMUNE-1, CEACIDE, Pretarget, NovoMAb-G2, TNT, Gliomab-H, GNI-250, EMD-72000, LymphoCide, CMA 676, Monopharm-C, 4B5, ior egf.r3, ior c5, BABS, anti-FLK-2, MDX-260, ANA Ab, SMART 1D10 Ab, SMART ABL 364 Ab and ImmuRAIT-CEA, but it is not so limited.

The cancer vaccine may be selected from the group consisting of EGF, Anti-idiotypic cancer vaccines, Gp75 antigen, GMK melanoma vaccine, MGV ganglioside conjugate vaccine, Her2/neu, Ovarex, M-Vax, O-Vax, L-Vax, STn-KHL theratope, BLP25 (MUC-1), liposomal idiotypic vaccine, Melacine, peptide antigen vaccines, toxin/antigen vaccines, MVA-based vaccine, PACIS, BCG vaccine, TA-HPV, TA-CIN, DISC-virus and ImmuCyst/TheraCys, but it is not so limited.

As used herein, the terms "cancer antigen" and "tumor antigen" are used interchangeably to refer to antigens which are differentially expressed by cancer cells and can thereby be exploited in order to target cancer cells. Cancer antigens are antigens which can potentially stimulate apparently tumor-specific immune responses. Some of these antigens are encoded, although not necessarily expressed, by normal cells. These antigens can be characterized as those which are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), fusion proteins resulting from internal deletions or chromosomal translocations. Still other cancer antigens can be encoded by viral genes such as those carried on RNA and DNA tumor viruses.

The immunomodulatory oligonucleotides of the invention can in some aspects also be used to treat or prevent infections by viruses, bacteria, fungi, or parasites. A subject having an infection is a subject that has been exposed to an infectious pathogen and has acute or chronic detectable levels of the pathogen in the body. The immunomodulatory oligonucleotides can be used with or without an antigen to mount an antigen specific systemic or mucosal immune response that is capable of reducing the level of or eradicating the infectious pathogen. An infectious disease, as used herein, is a disease arising from the presence of a foreign microorganism in the body. It is particularly important to develop effective vaccine strategies and treatments to protect the body's mucosal surfaces, which are the primary site of pathogenic entry.

Viruses are small infectious agents which generally contain a nucleic acid core and a protein coat, but are not independently living organisms. Viruses can also take the form of infectious nucleic acids lacking a protein. A virus cannot survive in the absence of a living cell within which it can replicate. Viruses enter specific living cells either by endocytosis or direct injection of DNA (phage) and multiply, causing disease. The multiplied virus can then be released and infect additional cells. Some viruses are DNA-containing viruses and others are RNA-containing viruses. DNA viruses include Pox, Herpes, Adeno, Papova, Parvo, and Hepadna. RNA viruses include Picorna, Calici, Astro, Toga, Flavi, Corona, Paramyxo, Orthomyxo, Bunya, Arena, Rhabdo, Filo, Borna, Reo, and Retro. In some aspects, the invention also intends to treat diseases in which prions are implicated in disease progression such as for example bovine spongiform encephalopathy (i.e., mad cow disease, BSE) or scrapie infection in animals, or Creutzfeldt-Jakob disease in humans.

Viruses include, but are not limited to, enteroviruses (including, but not limited to, viruses that the family picornaviridae, such as polio virus, Coxsackie virus, echo virus), rotaviruses, adenovirus, and hepatitis virus, such as hepatitis A, B, C D and E. Specific examples of viruses that have been found in humans include but are not limited to: Retroviridae (e.g., human immunodeficiency viruses, such as HIV-1 (also referred to as HTLV-III, LAV or HTLV-III/LAV, or HIV-III; and other isolates, such as HIV-LP; Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bunyaviridae (e.g., Hantaan viruses, bunya viruses, phleboviruses and Nairo viruses); Arenaviridae (hemorrhagic fever viruses); Reoviridae (e.g., reoviruses, orbiviurses and rotaviruses); Birnaviridae; Hepadnaviridae (Hepatitis B virus); Parvoviridae (parvoviruses); Papovaviridae (papillomaviruses, polyoma viruses); Adenoviridae (most adenoviruses); Herpesviridae (herpes simplex virus (HSV) 1 and 2, varicella zoster virus, cytomegalovirus (CMV)); Poxviridae (variola viruses, vaccinia viruses, pox viruses); Iridoviridae (e.g., African swine fever virus); and other viruses acute laryngotracheobronchitis virus, Alphavirus, Kaposi's sarcoma-associated herpesvirus, Newcastle disease virus, Nipah virus, Norwalk virus, Papillomavirus, parainfluenza virus, avian influenza, SARs virus, West Nile virus.

Viral hepatitis is an inflammation of the liver which may produce swelling, tenderness, and sometimes permanent damage to the liver. If the inflammation of the liver continues at least six months or longer, it is referred to as chronic hepatitis. There are at least five different viruses known to cause viral hepatitis, include hepatitis A, B, C D and E. Hepatitis A is generally communicated through food or drinking water contaminated with human feces. Hepatitis B generally is spread through bodily fluids such as blood. For instance, it may be spread from mother to child at birth, through sexual contact, contaminated blood transfusions and needles. Hepatitis C is quite common and like Hepatitis B is often spread through blood transfusions and contaminated needles. Hepatitis D is found most often in IV drug users who are carriers of the hepatitis B virus with which it co-associates. Hepatitis E is similar to viral hepatitis A and is generally associated with poor sanitation.

Both gram negative and gram positive bacteria serve as antigens in vertebrate animals. Such gram positive bacteria include, but are not limited to, *Pasteurella* species, *Staphylococci* species, and *Streptococcus* species. Gram negative bacteria include, but are not limited to, *Escherichia coli, Pseudomonas* species, and *Salmonella* species. Specific examples of infectious bacteria include but are not limited to, *Helicobacter pyloris, Borelia burgdorferi, Legionella pneumophilia, Mycobacteria* sps (e.g. *M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyogenes* (Group A *Streptococcus), Streptococcus agalactiae* (Group B *Streptococcus), Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus antracis, corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira, Rickettsia,* and *Actinomyces israelli.*

Examples of fungi include *Cryptococcus neoformans, Histoplasma capsulatum, Coccidioides immitis, Blastomyces dermatitidis, Chlamydia trachomatis, Candida albicans.*

Other infectious organisms (i.e., protists) include *Plasmodium* spp. such as *Plasmodium falciparum, Plasmodium malariae, Plasmodium ovale,* and *Plasmodium vivax* and *Toxoplasma gondii.* Blood-borne and/or tissues parasites include *Plasmodium* spp., *Babesia microti, Babesia divergens, Leishmania tropica, Leishmania* spp., *Leishmania braziliensis, Leishmania donovani, Trypanosoma gambiense* and *Trypanosoma rhodesiense* (African sleeping sickness), *Trypanosoma cruzi* (Chagas' disease), and *Toxoplasma gondii.*

Other medically relevant microorganisms have been described extensively in the literature, e.g., see C. G. A Thomas, Medical Microbiology, Bailliere Tindall, Great Britain 1983, the entire contents of which is hereby incorporated by reference.

The oligonucleotides of the invention may be administered to a subject with an anti-microbial agent. An anti-microbial agent, as used herein, refers to a naturally-occurring or synthetic compound which is capable of killing or inhibiting infectious microorganisms. The type of anti-microbial agent useful according to the invention will depend upon the type of microorganism with which the subject is infected or at risk of becoming infected. Anti-microbial agents include but are not limited to anti-bacterial agents, anti-viral agents, anti-fungal agents and anti-parasitic agents. Phrases such as "anti-infective agent", "anti-bacterial agent", "anti-viral agent", "anti-fungal agent", "anti-parasitic agent" and "parasiticide" have well-established meanings to those of ordinary skill in the art and are defined in standard medical texts. Briefly, anti-bacterial agents kill or inhibit bacteria, and include antibiotics as well as other synthetic or natural compounds having similar functions. Antibiotics are low molecular weight molecules which are produced as secondary metabolites by cells, such as microorganisms. In general, antibiotics interfere with one or more bacterial functions or structures which are specific for the microorganism and which are not present in host cells. Anti-viral agents can be isolated from natural sources or synthesized and are useful for killing or inhibiting viruses.

Anti-fungal agents are used to treat superficial fungal infections as well as opportunistic and primary systemic fungal infections. Anti-parasite agents kill or inhibit parasites.

Examples of anti-parasitic agents, also referred to as parasiticides useful for human administration include but are not limited to albendazole, amphotericin B, benznidazole, bithionol, chloroquine HCl, chloroquine phosphate, clindamycin, dehydroemetine, diethylcarbamazine, diloxanide furoate, eflornithine, furazolidaone, glucocorticoids, halofantrine, iodoquinol, ivermectin, mebendazole, mefloquine, meglumine antimoniate, melarsoprol, metrifonate, metronidazole, niclosamide, nifurtimox, oxamniquine, paromomycin, pentamidine isethionate, piperazine, praziquantel, primaquine phosphate, proguanil, pyrantel pamoate, pyrimethanmine-sulfonamides, pyrimethanmine-sulfadoxine, quinacrine HCl, quinine sulfate, quinidine gluconate, spiramycin, stibogluconate sodium (sodium antimony gluconate), suramin, tetracycline, doxycycline, thiabendazole, tinidazole, trimethroprim-sulfamethoxazole, and tryparsamide some of which are used alone or in combination with others.

Antibacterial agents kill or inhibit the growth or function of bacteria. A large class of antibacterial agents is antibiotics. Antibiotics, which are effective for killing or inhibiting a wide range of bacteria, are referred to as broad spectrum antibiotics. Other types of antibiotics are predominantly effective against the bacteria of the class gram-positive or gram-negative. These types of antibiotics are referred to as narrow spectrum antibiotics. Other antibiotics which are effective against a single organism or disease and not against other types of bacteria, are referred to as limited spectrum antibiotics. Antibacterial agents are sometimes classified based on their primary mode of action. In general, antibacterial agents are cell wall synthesis inhibitors, cell membrane inhibitors, protein synthesis inhibitors, nucleic acid synthesis or functional inhibitors, and competitive inhibitors.

Antiviral agents are compounds which prevent infection of cells by viruses or replication of the virus within the cell. There are many fewer antiviral drugs than antibacterial drugs because the process of viral replication is so closely related to DNA replication within the host cell, that non-specific antiviral agents would often be toxic to the host. There are several stages within the process of viral infection which can be blocked or inhibited by antiviral agents. These stages include, attachment of the virus to the host cell (immunoglobulin or binding peptides), uncoating of the virus (e.g. amantadine), synthesis or translation of viral mRNA (e.g. interferon), replication of viral RNA or DNA (e.g. nucleotide analogues), maturation of new virus proteins (e.g. protease inhibitors), and budding and release of the virus.

Nucleotide analogues are synthetic compounds which are similar to nucleotides, but which have an incomplete or abnormal deoxyribose or ribose group. Once the nucleotide analogues are in the cell, they are phosphorylated, producing the triphosphate formed which competes with normal nucleotides for incorporation into the viral DNA or RNA. Once the triphosphate form of the nucleotide analogue is incorporated into the growing nucleic acid chain, it causes irreversible association with the viral polymerase and thus chain termination. Nucleotide analogues include, but are not limited to, acyclovir (used for the treatment of herpes simplex virus and varicella-zoster virus), gancyclovir (useful for the treatment of cytomegalovirus), idoxuridine, ribavirin (useful for the treatment of respiratory syncitial virus), dideoxyinosine, dideoxycytidine, zidovudine (azidothymidine), imiquimod, and resimiquimod.

The interferons are cytokines which are secreted by virus-infected cells as well as immune cells. The interferons function by binding to specific receptors on cells adjacent to the infected cells, causing the change in the cell which protects it from infection by the virus. α and β-interferon also induce the expression of Class I and Class II MHC molecules on the surface of infected cells, resulting in increased antigen presentation for host immune cell recognition. α and β-interferons are available as recombinant forms and have been used for the treatment of chronic hepatitis B and C infection. At the dosages which are effective for anti-viral therapy, interferons have severe side effects such as fever, malaise and weight loss.

Anti-viral agents useful in the invention include but are not limited to immunoglobulins, amantadine, interferons, nucleotide analogues, and protease inhibitors. Specific examples of anti-virals include but are not limited to Acemannan; Acyclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscarnet Sodium; Fosfonet Sodium; Ganciclovir; Ganciclovir Sodium; Idoxuridine; Kethoxal; Lamivudine; Lobucavir; Memotine Hydrochloride; Methisazone; Nevirapine; Penciclovir; Pirodavir; Ribavirin; Rimantadine Hydrochloride; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; and Zinviroxime.

Anti-fungal agents are useful for the treatment and prevention of infective fungi. Anti-fungal agents are sometimes classified by their mechanism of action. Some anti-fungal agents function as cell wall inhibitors by inhibiting glucose synthase. These include, but are not limited to, basiungin/ECB. Other anti-fungal agents function by destabilizing membrane integrity. These include, but are not limited to, immidazoles, such as clotrimazole, sertaconzole, fluconazole, itraconazole, ketoconazole, miconazole, and voriconacole, as well as FK 463, amphotericin B, BAY 38-9502, MK 991, pradimicin, UK 292, butenafine, and terbinafine. Other anti-fungal agents function by breaking down chitin (e.g. chitinase) or immunosuppression (501 cream).

The immunomodulatory oligonucleotides may also be useful for treating and preventing autoimmune disease. Autoimmune disease is a class of diseases in which a subject's own antibodies react with host tissue or in which immune effector T cells are autoreactive to endogenous self peptides and cause destruction of tissue. Thus an immune response is mounted against a subject's own antigens, referred to as self antigens. Autoimmune diseases include but are not limited to alopecia areata, acquired hemophilia, ankylosing spondylitis, antiphospholipid syndrome, autoimmune-associated infertility, autoimmune encephalomyelitis, autoimmune hepatitis, autoimmune hemolytic anemia, autoimmune diabetes mellitus, autoimmune thrombocytopenic purpura, Behcet's syndrome, bullous pemphigoid, cardiomyopathy, chronic fatigue immune dysfunction syndrome (CFIDS), chronic inflammatory demyelinating polyneuropathy, Churg-Strauss syndrome, cicatricial pemphigoid, CREST syndrome, cold agglutinin disease, dermatomyositis, discoid lupus, essential mixed cryoglobulinemia, fibromyalgia, fibromyositis, Guillain-Barré syndrome, Hashimoto's thyroiditis, glomerulonephritis (e.g., crescentic glomerulonephritis, proliferative glomerulonephritis), Grave's disease, graft versus host disease, Goodpasture's syndrome, pemphigus (e.g., pemphigus vulgaris), idiopathic pulmonary fibrosis, idiopathic thrombocytopenic purpura, insulin resistance, idiopathic Addison's disease, IgA nephropathy, inflammatory bowel disease (including Crohn's disease and ulcerative colitis), juvenile arthritis, lichen planus, myasthenia gravis, multiple sclerosis, mixed connective tissue disease, polymyositis, pernicious anemia, polyarteritis nodosa, polychondritis, polyglandular syndromes, polymyalgia rheumatica, primary agammaglobulinemia, primary biliary cirrhosis, psoriasis, Raynaud's phenomena, Reiter's syndrome, juvenile and adult rheumatoid arthritis, Sjorgen's syndrome, scleroderma with anti-collagen antibodies, sarcoidosis, stiff-man syndrome, systemic lupus erythematosus (SLE), Takayasu arthritis, transplanted organ rejection, temporal arteritis/giant cell arteritis, uveitis, ulcerative colitis, vasculitis, and vitiligo.

A "self-antigen" as used herein refers to an antigen of a normal host tissue. Normal host tissue does not include cancer cells. Thus an immune response mounted against a self-antigen, in the context of an autoimmune disease, is an undesirable immune response and contributes to destruction and damage of normal tissue, whereas an immune response mounted against a cancer antigen is a desirable immune response and contributes to the destruction of the tumor or cancer. Thus, in some aspects of the invention aimed at treating autoimmune disorders it is not recommended that the immunomodulatory oligonucleotides be administered with self antigens, particularly those that are the targets of the autoimmune disorder.

In other instances, the immunomodulatory oligonucleotides may be delivered with low doses of self-antigens. A number of animal studies have demonstrated that mucosal administration of low doses of antigen can result in a state of immune hyporesponsiveness or "tolerance." The active mechanism appears to be a cytokine-mediated immune deviation away from a Th1 towards a predominantly Th2 and Th3 (i.e., TGF-β dominated) response. The active suppression with low dose antigen delivery can also suppress an unrelated immune response (bystander suppression) which is of considerable interest in the therapy of autoimmune diseases, for example, rheumatoid arthritis and SLE. Bystander suppression involves the secretion of Th1-counter-regulatory, suppressor cytokines in the local environment where proinflammatory and Th1 cytokines are released in either an antigen-specific or antigen-nonspecific manner. "Tolerance" as used herein is used to refer to this phenomenon. Indeed, oral tolerance has been effective in the treatment of a number of autoimmune diseases in animals including: experimental autoimmune encephalomyelitis (EAE), experimental autoimmune myasthenia gravis, collagen-induced arthritis (CIA), and insulin-dependent diabetes mellitus. In these models, the prevention and suppression of autoimmune disease is associated with a shift in antigen-specific humoral and cellular responses from a Th1 to Th2/Th3 response.

The immunomodulatory oligonucleotides of the invention are useful in some aspects for treating an inflammatory disorder. As used herein, the term "inflammatory disorder" refers to a condition associated with an antigen-nonspecific reaction of the innate immune system that involves accumulation and activation of leukocytes and plasma proteins at a site of infection, toxin exposure, or cell injury. Cytokines that are characteristic of inflammation include tumor necrosis factor (TNF-α), interleukin 1 (IL-1), IL-6, IL-12, interferon alpha (IFN-α), interferon beta (IFN-β), and chemokines. Thus, certain types of asthma, allergy, and autoimmune disorders may have characteristics of an inflammatory disorder.

Inflammatory disorders also include, for example cardiovascular disease, chronic obstructive pulmonary disease (COPD), bronchiectasis, chronic cholecystitis, tuberculosis, Hashimoto's thyroiditis, sepsis, sarcoidosis, silicosis and other pneumoconioses, and an implanted foreign body in a wound, but are not so limited. As used herein, the term "sepsis" refers to a well-recognized clinical syndrome associated with a host's systemic inflammatory response to microbial invasion. The term "sepsis" as used herein refers to a condition that is typically signaled by fever or hypothermia, tachycardia, and tachypnea, and in severe instances can progress to hypotension, organ dysfunction, and even death.

A "subject" shall mean a human or vertebrate animal including but not limited to a dog, cat, horse, cow, pig, sheep, goat, turkey, chicken, primate, e.g., monkey, and fish (aquaculture species), e.g. salmon. Thus, the invention can also be used to treat cancer and tumors, infections, and allergy/asthma in non human subjects. For example, cancer is one of the leading causes of death in companion animals (i.e., cats and dogs).

As used herein, the term treat, treated, or treating when used with respect to an disorder such as an infectious disease, cancer, allergy, or asthma refers to a prophylactic treatment which increases the resistance of a subject to development of the disease (e.g., to infection with a pathogen) or, in other words, decreases the likelihood that the subject will develop the disease (e.g., become infected with the pathogen) as well as a treatment after the subject has developed the disease in order to fight the disease (e.g., reduce or eliminate the infection) or prevent the disease from becoming worse.

In the instances when the immunomodulatory oligonucleotide is administered with an antigen, the subject may be exposed to the antigen. As used herein, the term exposed to refers to either the active step of contacting the subject with an antigen or the passive exposure of the subject to the antigen in vivo. Methods for the active exposure of a subject to an antigen are well-known in the art. In general, an antigen is administered directly to the subject by any means such as intravenous, intramuscular, oral, transdermal, mucosal, intranasal, intratracheal, or subcutaneous administration. The antigen can be administered systemically or locally. Methods for administering the antigen and the immunomodulatory oligonucleotide are described in more detail below. A subject is passively exposed to an antigen if an antigen becomes available for exposure to the immune cells in the body. A subject may be passively exposed to an antigen, for instance, by entry of a foreign pathogen into the body or by the development of a tumor cell expressing a foreign antigen on its surface. The antigen or allergen in some embodiments is conjugated to the oligonucleotide.

The methods in which a subject is passively exposed to an antigen can be particularly dependent on timing of administration of the immunomodulatory oligonucleotide. For instance, in a subject at risk of developing a cancer or an infectious disease or an allergic or asthmatic response, the subject may be administered the Immunomodulatory oligonucleotide on a regular basis when that risk is greatest, i.e., during allergy season or after exposure to a cancer causing agent. Additionally the Immunomodulatory oligonucleotide may be administered to travelers before they travel to foreign lands where they are at risk of exposure to infectious agents. Likewise the Immunomodulatory oligonucleotide may be administered to soldiers or civilians at risk of exposure to biowarfare to induce a systemic or mucosal immune response to the antigen when and if the subject is exposed to it.

An antigen as used herein is a molecule capable of provoking an immune response. Antigens include but are not limited to cells, cell extracts, proteins, polypeptides, peptides, polysaccharides, polysaccharide conjugates, peptide and non-peptide mimics of polysaccharides and other molecules, small molecules, lipids, glycolipids, carbohydrates, viruses and viral extracts and multicellular organisms such as parasites and allergens. The term antigen broadly includes any type of molecule which is recognized by a host immune system as being foreign. Antigens include but are not limited to cancer antigens, microbial antigens, and allergens.

A cancer antigen as used herein is a compound, such as a peptide or protein, associated with a tumor or cancer cell surface and which is capable of provoking an immune response when expressed on the surface of an antigen presenting cell in the context of an MHC molecule. Cancer antigens can be prepared from cancer cells either by preparing crude extracts of cancer cells, for example, as described in Cohen, et al., 1994, *Cancer Research*, 54:1055, by partially purifying the antigens, by recombinant technology, or by de novo synthesis of known antigens. Cancer antigens include but are not limited to antigens that are recombinantly expressed, an immunogenic portion of, or a whole tumor or cancer. Such antigens can be isolated or prepared recombinantly or by any other means known in the art.

A microbial antigen as used herein is an antigen of a microorganism and includes but is not limited to virus, bacteria, parasites, and fungi. Such antigens include the intact microorganism as well as natural isolates and fragments or derivatives thereof and also synthetic compounds which are identical to or similar to natural microorganism antigens and induce an immune response specific for that microorganism. A compound is similar to a natural microorganism antigen if it induces an immune response (humoral and/or cellular) to a natural microorganism antigen. Such antigens are used routinely in the art and are well known to those of ordinary skill in the art.

An allergen refers to a substance (antigen) that can induce an allergic or asthmatic response in a susceptible subject. The list of allergens is enormous and can include pollens, insect venoms, animal dander dust, fungal spores and drugs (e.g. penicillin). Examples of natural, animal and plant allergens include but are not limited to proteins specific to the following genuses: *Canine* (*Canis familiaris*); *Dermatophagoides* (e.g. *Dermatophagoides farinae*); *Felis* (*Felis domesticus*); *Ambrosia* (*Ambrosia artemiisfolia*; *Lolium* (e.g. *Lolium perenne* or *Lolium multiflorum*); *Cryptomeria* (*Cryptomeria japonica*); *Alternaria* (*Alternaria alternata*); *Alder, Alnus* (*Alnus gultinoasa*); *Betula* (*Betula verrucosa*); *Quercus* (*Quercus alba*); *Olea* (*Olea europa*); *Artemisia* (*Artemisia vulgaris*); *Plantago* (e.g. *Plantago lanceolata*); *Parietaria* (e.g. *Parietaria officinalis* or *Parietaria judaica*); *Blattella* (e.g. *Blattella germanica*); *Apis* (e.g. *Apis multiflorum*); *Cupressus* (e.g. *Cupressus sempervirens, Cupressus arizonica* and *Cupressus macrocarpa*); *Juniperus* (e.g. *Juniperus sabinoides, Juniperus virginiana, Juniperus communis* and *Juniperus ashen*); *Thuya* (e.g. *Thuya orientalis*); *Chamaecyparis* (e.g. *Chamaecyparis obtusa*); *Periplaneta* (e.g. *Periplaneta americana*); *Agropyron* (e.g. *Agropyron repens*); *Secale* (e.g. *Secale cereale*); *Triticum* (e.g. *Triticum aestivum*); *Dactylis* (e.g. *Dactylis glomerata*); *Festuca* (e.g. *Festuca elation*); *Poa* (e.g. *Poa pratensis* or *Poa compressa*); *Avena* (e.g. *Avena sativa*); *Holcus* (e.g. *Holcus lanatus*); *Anthoxanthum* (e.g. *Anthoxanthum odoratum*); *Arrhenatherum* (e.g. *Arrhenatherum elatius*); *Agrostis* (e.g. *Agrostis alba*); *Phleum* (e.g. *Phleum pratense*); *Phalaris* (e.g. *Phalaris arundinacea*); *Paspalum* (e.g. *Paspalum notatum*); *Sorghum* (e.g. *Sorghum halepensis*); and *Bromus* (e.g. *Bromus inermis*).

The term substantially purified as used herein refers to a polypeptide which is substantially free of other proteins, lipids, carbohydrates or other materials with which it is naturally associated. One skilled in the art can purify viral or bacterial polypeptides using standard techniques for protein purification. The substantially pure polypeptide will often yield a single major band on a non-reducing polyacrylamide gel. In the case of partially glycosylated polypeptides or those that have several start codons, there may be several bands on a non-reducing polyacrylamide gel, but these will form a distinctive pattern for that polypeptide. The purity of the viral or bacterial polypeptide can also be determined by amino-terminal amino acid sequence analysis. Other types of antigens not encoded by a nucleic acid vector such as polysaccharides, small molecule, mimics etc are included within the invention.

The immunomodulatory oligonucleotides can be combined with other therapeutic agents such as adjuvants to enhance immune responses. The immunomodulatory oligonucleotide and other therapeutic agent may be administered simultaneously or sequentially. When the other therapeutic agents are administered simultaneously they can be administered in the same or separate formulations, but are administered at the same time. The other therapeutic agents are administered sequentially with one another and with an immunomodulatory oligonucleotide, when the administration of the other therapeutic agents and the immunomodulatory oligonucleotide is temporally separated. The separation in time between the administrations of these compounds may be a matter of minutes or it may be longer. Other therapeutic agents include but are not limited to adjuvants, cytokines, antibodies, antigens, etc.

The compositions of the invention may also be administered with non-nucleic acid adjuvants. A non-nucleic acid adjuvant is any molecule or compound except for the immunomodulatory oligonucleotides described herein which can stimulate the humoral and/or cellular immune response. Non-nucleic acid adjuvants include, for instance, adjuvants that create a depo effect, immune stimulating adjuvants, and adjuvants that create a depo effect and stimulate the immune system.

The immunomodulatory oligonucleotides are in some embodiments also useful as mucosal adjuvants. It has previously been discovered that both systemic and mucosal immunity are induced by mucosal delivery of CpG oligonucleotides. Thus, the oligonucleotides may be administered in combination with other mucosal adjuvants.

Immune responses can also be induced or augmented by the co-administration or co-linear expression of cytokines (Bueler & Mulligan, 1996; Chow et al., 1997; Geissler et al., 1997; Iwasaki et al., 1997; Kim et al., 1997) or B-7 co-stimulatory molecules (Iwasaki et al., 1997; Tsuji et al., 1997) with the immunomodulatory oligonucleotides. The term cytokine is used as a generic name for a diverse group of soluble proteins and peptides which act as humoral regulators at nano- to picomolar concentrations and which, either under normal or pathological conditions, modulate the functional activities of individual cells and tissues. These proteins also mediate interactions between cells directly and regulate processes taking place in the extracellular environment. Examples of cytokines include, but are not limited to IL-1, IL-2, IL-4, IL-5, IL-6, IL-7, IL-10, IL-12, IL-15, IL-18, granulocyte-macrophage colony stimulating factor (GM-CSF), granulocyte colony stimulating factor (G-CSF), interferon-γ (γ-IFN), IFN-α, tumor necrosis factor (TNF), TGF-β, FLT-3 ligand, and CD40 ligand.

The oligonucleotides are also useful for redirecting an immune response from a Th2 immune response to a Th1 immune response. This results in the production of a relatively balanced Th1/Th2 environment. Redirection of an immune response from a Th2 to a Th1 immune response can be assessed by measuring the levels of cytokines produced in response to the oligonucleotide (e.g., by inducing monocytic cells and other cells to produce Th1 cytokines, including IL-12, IFN-γ and GM-CSF). The redirection or rebalance of the immune response from a Th2 to a Th1 response is particularly useful for the treatment or prevention of asthma. For instance, an effective amount for treating asthma can be that amount; useful for redirecting a Th2 type of immune response that is associated with asthma to a Th1 type of response or a balanced Th1/Th2 environment. Th2 cytokines, especially IL-4 and IL-5 are elevated in the airways of asthmatic subjects. The immunomodulatory oligonucleotides of the invention cause an increase in Th1 cytokines which helps to rebalance the immune system, preventing or reducing the adverse effects associated with a predominately Th2 immune response.

The oligonucleotides of the invention may also be useful for treating airway remodeling. Airway remodeling results from smooth muscle cell proliferation and/or submucosal thickening in the airways, and ultimately causes narrowing of the airways leading to restricted airflow. The oligonucleotides of the invention may prevent further remodeling and possibly even reduce tissue build up resulting from the remodeling process.

The oligonucleotides are also useful for improving survival, differentiation, activation and maturation of dendritic cells. The immunomodulatory oligonucleotides have the unique capability to promote cell survival, differentiation, activation and maturation of dendritic cells.

Immunomodulatory oligonucleotides also increase natural killer cell lytic activity and antibody dependent cellular cytotoxicity (ADCC). ADCC can be performed using a immunomodulatory oligonucleotide in combination with an antibody specific for a cellular target, such as a cancer cell. When the immunomodulatory oligonucleotide is administered to a subject in conjunction with the antibody the subject's immune system is induced to kill the tumor cell. The antibodies useful in the ADCC procedure include antibodies which interact with a cell in the body. Many such antibodies specific for cellular targets have been described in the art and many are commercially available.

The invention also includes a method for inducing antigen non-specific innate immune activation and broad spectrum resistance to infectious challenge using the immunomodulatory oligonucleotides. The term antigen non-specific innate immune activation as used herein refers to the activation of immune cells other than B cells and for instance can include the activation of NK cells, T cells or other immune cells that can respond in an antigen independent fashion or some combination of these cells. A broad spectrum resistance to infectious challenge is induced because the immune cells are in active form and are primed to respond to any invading compound or microorganism. The cells do not have to be specifically primed against a particular antigen. This is particularly useful in biowarfare, and the other circumstances described above such as travelers.

The immunostimulatory ODN of the invention may be combined with a cationic lipid. In one embodiment the cationic lipid is DOTAP (N-[1-(2,3-dioleoyloxy)propyl]-N,N,N-trimethylammonium methyl-sulfate). DOTAP is believed to transport polymers into cells and specifically traffic to the endosomal compartment, where it can release the polymer in a pH-dependent fashion. Once in the endosomal compartment, the polymers can interact with certain intracellular TLRs, triggering TLR-mediated signal transduction pathways involved in generating an immune response. Other agents with similar properties including trafficking to the endosomal compartment can be used in place of or in addition to DOTAP. Other lipid formulations include, for example, EFFECTENE® (a non-liposomal lipid with a special DNA condensing enhancer) and SUPERFECT® (a novel acting dendrimeric technology), SMARTICLES® (charge reversible particles that become positively charged when they cross cell membranes) and Stable Nucleic Acid Lipid Particles (SNALPs) which employ a lipid bilayer. Liposomes are commercially available from Gibco BRL, for example, as LIPOFECTIN® and LIPOFECTACE™, which are formed of cationic lipids such as N-[1-(2,3 dioleyloxy)-propyl]-N,N,N-trimethylammonium chloride (DOTMA) and dimethyl dioctadecylammonium bromide (DDAB). Methods for making liposomes are well known in the art and have been described in many publications. Liposomes also have been reviewed by Gregoriadis G (1985) *Trends Biotechnol* 3:235-241. In other embodiments the immunostimulatory polymers of the invention are combined with microparticles, cyclodextrins, nanoparticles, niosomes, dendrimers, polycytionic peptides, virosomes and virus-like particles, or ISCOMS®.

The immunomodulatory oligonucleotides may be directly administered to the subject or may be administered in conjunction with an oligonucleotide delivery complex. An oligonucleotide delivery complex shall mean an oligonucleotide molecule associated with (e.g. ionically or covalently bound to; or encapsulated within) a targeting means (e.g. a molecule that results in higher affinity binding to target cell. Examples of oligonucleotide delivery complexes include oligonucleotides associated with a sterol (e.g. cholesterol), a lipid (e.g. a cationic lipid, virosome or liposome), or a target cell specific binding agent (e.g. a ligand recognized by target cell specific receptor). Preferred complexes may be sufficiently stable in vivo to prevent significant uncoupling prior to internalization by the target cell. However, the complex can be cleavable under appropriate conditions within the cell so that the oligonucleotide is released in a functional form.

Delivery vehicles or delivery devices for delivering antigen and oligonucleotides to surfaces have been described. The immunomodulatory oligonucleotide and/or the antigen and/or other therapeutics may be administered alone (e.g., in saline or buffer) or using any delivery vehicles known in the art. For instance the following delivery vehicles have been described: cochleates; Emulsomes®; certain cationic lipids such as those mentioned above e.g. ISCOM®s; live bacterial vectors (e.g., *Salmonella, Escherichia coli, Bacillus* Calmette-Guérin, *Shigella, Lactobacillus*); live viral vectors (e.g., Vaccinia, adenovirus, Herpes Simplex); microspheres; nucleic acid vaccines; polymers (e.g. carboxymethylcellulose, chitosan); polymer rings; proteosomes; sodium fluoride; transgenic plants. In some embodiments of the invention the delivery vehicle is a liposome, a niosome, a lipoplexe, a polyplexe, a lipopolyplexe, a water-in-oil (W/O) emulsion, an oil-in-water (O/W) emulsion, a water-in-oil-in water (W/O/W) multiple emulsion, a micro-emulsion, a nano-emulsion, a micelle, a dendrimer, a virosome, a virus-like particle, a polymeric nanoparticle, as a nanosphere or a nanocapsule, a polymeric microparticle, such as a microsphere or a microcapsule. Other delivery vehicles are known in the art.

The term "effective amount" of an immunomodulatory oligonucleotide refers to the amount necessary or sufficient to realize a desired biologic effect. For example, an effective amount of an immunomodulatory oligonucleotide administered with an antigen for inducing mucosal immunity is that amount necessary to cause the development of IgA in response to an antigen upon exposure to the antigen, whereas that amount required for inducing systemic immunity is that amount necessary to cause the development of IgG in response to an antigen upon exposure to the antigen. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject. The effective amount for any particular application can vary depending on such factors as the disease or condition being treated, the particular an immunomodulatory oligonucleotide being administered the size of the subject, or the severity of the disease or condition. One of ordinary skill in the art can empirically determine the effective amount of a particular an immunomodulatory oligonucleotide and/or antigen and/or other therapeutic agent without necessitating undue experimentation.

Subject doses of the compounds described herein for mucosal or local delivery typically range from about 0.1 µg to 10 mg per administration, which depending on the application could be given daily, weekly, or monthly and any other amount of time therebetween. More typically mucosal or local doses range from about 10 µg to 5 mg per administration, and most typically from about 100 µg to 1 mg, with 2-4 administrations being spaced days or weeks apart. More typically, immune stimulant doses range from 1 µg to 10 mg per administration, and most typically 10 µg to 1 mg, with daily or weekly administrations. Subject doses of the compounds described herein for parenteral delivery for the purpose of inducing an antigen-specific immune response, wherein the compounds are delivered with an antigen but not another therapeutic agent are typically 5 to 10,000 times higher than the effective mucosal dose for vaccine adjuvant or immune stimulant applications, and more typically 10 to 1,000 times higher, and most typically 20 to 100 times higher. Doses of the compounds described herein for parenteral delivery for the purpose of inducing an innate immune response or for increasing ADCC or for inducing an antigen specific immune response when the immunomodulatory oligonucleotides are administered in combination with other therapeutic agents or in specialized delivery vehicles typically range from about 0.1 µg to 10 mg per administration, which depending on the application could be given daily, weekly, or monthly and any other amount of time therebetween. More typically parenteral doses for these purposes range from about 10 µg to 5 mg per administration, and most typically from about 100 µg to 1 mg, with 2-4 administrations being spaced days or weeks apart. In some embodiments, however, parenteral doses for these purposes may be used in a range of 5 to 10,000 times higher than the typical doses described above.

For any compound described herein the therapeutically effective amount can be initially determined from animal models. A therapeutically effective dose can also be determined from human data for oligonucleotides which have been tested in humans (human clinical trials have been initiated) and for compounds which are known to exhibit similar pharmacological activities, such as other adjuvants, e.g., LT and other antigens for vaccination purposes. Higher doses may be required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, an effective amount of the immunomodulatory oligonucleotide can be administered to a subject by any mode that delivers the oligonucleotide to the desired surface, e.g., mucosal, systemic. Administering the pharmaceutical composition of the present invention may be accomplished by any means known to the skilled artisan. Preferred routes of administration include but are not limited to oral, parenteral, intramuscular, intravenous, subcutaneous, intranasal, sublingual, intratracheal, inhalation, ocular, vaginal, and rectal.

For oral administration, the compounds (i.e., immunomodulatory oligonucleotides, antigens and other therapeutic agents) can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, i.e. EDTA for neutralizing internal acid conditions or may be administered without any carriers.

Also specifically contemplated are oral dosage forms of the above component or components. As demonstrated in the Examples below, the FANA-modified oligonucleotides have increased stability in acidic environments making them useful for oral application. The component or components may have additional chemical modifications such that oral delivery is even more efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, 1981, "Soluble Polymer-Enzyme Adducts" In: Enzymes as Drugs, Hocenberg and Roberts, eds., Wiley-Interscience, New York, N.Y., pp. 367-383; Newmark, et al., 1982, J. Appl. Biochem. 4:185-189. Other polymers that could be used are poly-1,3-dioxolane and poly-1,3,6-tioxocane. Preferred for pharmaceutical usage, as indicated above, are polyethylene glycol moieties.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the oligonucleotide (or derivative) or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the oligonucleotide (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the oligonucleotide or derivative either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

Also contemplated herein is pulmonary delivery of the oligonucleotides (or derivatives thereof). The oligonucleotide (or derivative) is delivered to the lungs of a mammal while inhaling and traverses across the lung epithelial lining to the blood stream. Other reports of inhaled molecules include Adjei et al., 1990, Pharmaceutical Research, 7:565-569; Adjei et al., 1990, International Journal of Pharmaceutics, 63:135-144 (leuprolide acetate); Braquet et al., 1989, Journal of Cardiovascular Pharmacology, 13(suppl. 5):143-146 (endothelin-1); Hubbard et al., 1989, Annals of Internal Medicine, Vol. III, pp. 206-212 (a1-antitrypsin); Smith et al., 1989, J. Clin. Invest. 84:1145-1146 (a-1-proteinase); Oswein et al., 1990, "Aerosolization of Proteins", Proceedings of Symposium on Respiratory Drug Delivery II, Keystone, Colo., March, (recombinant human growth hormone); Debs et al., 1988, J. Immunol. 140:3482-3488 (interferon-g and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of oligonucleotide (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified oligonucleotide may also be prepared in different formulations depending on the type of chemical modification or the type of device employed.

Formulations suitable for use with a nebulizer, either jet or ultrasonic, will typically comprise oligonucleotide (or derivative) dissolved in water at a concentration of about 0.1 to 25 mg of biologically active oligonucleotide per mL of solution. The formulation may also include a buffer and a simple sugar (e.g., for oligonucleotide stabilization and regulation of osmotic pressure). The nebulizer formulation may also contain a surfactant, to reduce or prevent surface induced aggregation of the oligonucleotide caused by atomization of the solution in forming the aerosol.

Formulations for use with a metered-dose inhaler device will generally comprise a finely divided powder containing the oligonucleotide (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing oligonucleotide (or derivative) and may also include a bulking agent, such as lactose, sorbitol, sucrose, or mannitol in amounts which facilitate dispersal of the powder from the device, e.g., 50 to 90% by weight of the formulation. The oligonucleotide (or derivative) should most advantageously be prepared in particulate form with an average particle size of less than 10 mm (or microns), most preferably 0.5 to 5 mm, for most effective delivery to the distal lung.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, *Science* 249:1527-1533, 1990, which is incorporated herein by reference.

The an immunomodulatory oligonucleotides and optionally other therapeutics and/or antigens may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The pharmaceutical compositions of the invention contain an effective amount of an immunomodulatory oligonucleotide and optionally antigens and/or other therapeutic agents optionally included in a pharmaceutically-acceptable carrier. The term pharmaceutically-acceptable carrier means one or more compatible solid or liquid filler, diluents or encapsulating substances which are suitable for administration to a human or other vertebrate animal. The term carrier denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Materials and Methods

Oligodeoxynucleotides (ODN) and Reagents

Solid-Phase Synthesis of FANA-Modified Oligonucleotides (ODN)

Oligonucleotides were synthesized on an ÄKTA Oligopilot 10 DNA/RNA synthesizer (GE-Healthcare) on a 1 µmole scale using standard β-cyanoethyl phosphoramidite chemistry. Primersupport PS200 were purchased from GE-Healthcare (loading: 40 µmol/g). 5'-DMT-protected β-cyanoethyl phosphoramidites were used for the synthesis of oligo-2'-deoxynucleotides. The DMT-group was removed at the 5'-end of the synthesis.

Deprotection and Purification

The ODNs (Table 1) were deprotected and cleaved from solid support by treatment with concentrated aqueous ammonia (40° C., 4 h). Purification was achieved on a SOURCE 15Q anion exchange column (CV: 6 ml, GE Healthcare) with the following gradient system: Buffer A: 10 mM sodium hydroxide, pH 12; buffer B: 2.5 M sodium chloride, 10 mM sodium hydroxide, pH 12. gradient used depended on the oligonucleotide sequence. The chromatography system was an ÄKTA Purifier 10 with an Frac950 fraction collector (GE Healthcare). The product-containing fractions were desalted on a Biogel P4 column and lyophilized.

Analytics

The ODNs were analyzed on an Agilent 1100 HPLC system with the following modules: Micro vacuum-degaser (G1379A), binary pump (G1312A), well-plate sampler (G1367A), column oven (G1316A) and MWD (G1365B) which was coupled to a Bruker Esquire 3000+ ion trap mass spectrometer (negative mode): Column: Waters X-Bridge C18 2.5 μm 2.1×50 mm; column temperature 60° C.; UV-detection at 260 nm; flow: 0.2 mL/min; solvent A: 385 mM HFIP+14.4 mM TEA; solvent B: methanol; injection volume: 10 μL; gradient: 0 min: 5% B, 15 min: 17.5% B, 50 min 24% B, 65 min: 45% B.

Depurination Assays

ODN were dissolved in water to a final concentration of 250 μM. For each ODN three samples (20 μl) were prepared by mixing the ODN solution with water and 1N HCl obtaining ODN solutions with a final concentration of 1 μg/μl in 0.1N HCl. For each ODN a separate solution was prepared with a final ODN concentration of 1 μg/μl without HCl which were used as zero time point samples in the depurination experiment. HCl containing Samples were incubated at RT for 10, 240 and 1440 min. After incubation approximately 5.3 μl $NH_4OH$ (1%) was added to dissolve the precipitated ODN. Samples were analyzed by HPLC on a Waters Atlantis C18 3 μm column 2.1×150 mm using a gradient separation (solvent A: 100 mM TEAAc, solvent B: ACN; 0% B (0 min), 9% B (9 min), 40% B (25 min), 95% B (30 min), 95% B (35 min), 0% B (36 min), 0% B (50 min)) at 30° C. column temperature. Guanine was monitored at 274 nm UV. A standard curve was prepared by analyzing standard samples of known Guanine concentration. The actual Guanine concentration in the ODN samples was back calculated using the calibration curve obtained from the standard samples.

TLR Assays

HEK293 cells were transfected by electroporation with vectors expressing the respective human TLR and a 6×NF-κB-luciferase reporter plasmid. Stable transfectants ($3 \times 10^4$ cells/well) were incubated indicated amounts of ODN for 16 h at 37° C. in a humidified incubator. Each data point was done in triplicate. Cells were lysed and assayed for luciferase gene activity (using the BriteLite kit from Perkin-Elmer,

TABLE 1

Sample sequences of ODNs and characterization by ESI-TOF

| Seq. Id. No. | Sequence [5'-3'] | M.W.[a][Da] | M.W.[b][Da] |
|---|---|---|---|
| 1 | T*faG*T*C-G*T*T*T*T*T*T*T*T*T*T*T*T*T*T*T | 6364.2 | 6365.4 |
| 2 | T*G*faT*C-G*T*T*T*T*T*T*T*T*T*T*T*T*T*T*T | 6364.2 | 6365.8 |
| 3 | T*G*T*faC-G*T*T*T*T*T*T*T*T*T*T*T*T*T*T*T | 6364.2 | 6365.6 |
| 4 | T*G*T*C-faG*T*T*T*T*T*T*T*T*T*T*T*T*T*T*T | 6364.2 | 6365.9 |
| 5 | T*faG*T*C-faG*T*T*T*T*T*T*T*T*T*T*T*T*T*T*T | 6382.2 | 6383.8 |
| 6 | T*G*T*C-G*faT*T*T*T*T*T*T*T*T*T*T*T*T*T*T | 6364.2 | 6366.0 |
| 7 | T*G*T*C-G*T*faT*T*T*T*T*T*T*T*T*T*T*T*T*T | 6364.2 | 6365.4 |
| 8 | T*G*T*C-G*T*T*T*T*T*T*T*T*T*T*T*T*T*T*T | 6347.0 | 6346.2 |
| 9 | T*C*faG*T*C*G*T*T*T*T*C*G*G*C*G*C*G*C*C*G | 7065.7 | 7063.5 |
| 10 | T*C*G*T*C*faG*T*T*T*T*C*G*G*C*G*C*G*C*C*G | 7065.7 | 7063.6 |
| 11 | T*C*faG*T*C*faG*T*T*T*T*C*G*G*C*G*C*G*C*C*G | 7083.7 | 7081.6 |
| 12 | T*C*G*T*C*G*T*T*T*T*C*faG*faG*C*faG*C*faG*C*C*G | 7137.7 | 7136.1 |
| 13 | T*C*faG*T*C*faG*T*T*T*T*C*faG*faG*C*faG*C*faG*C*C*G | 7173.7 | 7172.3 |
| 14 | T*C*faG*T*C*faG*T*T*T*T*C*faG*faG*C*faG*C*faG*C*C*3mG | 7203.7 | 7201.2 |
| 15 | T*C*G*T*C*G*T*T*T*T*C*G*G*C*G*C*G*C*C*G | 7047.7 | 7048.0 |
| 16 | T*C*G*T*C*G*T*T*T*T*C*G*G*C*G*C*G*C*C*3mG | 7077.8 | 7076.4 |

[a]Calculated (free acid);
[b]Determined by LC-MS (ESI-TOF)

Zaventem, Belgium). Stimulation indices were calculated in reference to reporter gene activity of medium without addition of ODN.

Cell Purification

Peripheral blood buffy coat preparations from healthy human donors were obtained from the Blood Bank of the University of Düsseldorf (Germany) and PBMC were purified by centrifugation over Ficoll-Hypaque (Sigma). Cells were cultured in a humidified incubator at 37° C. in RPMI 1640 medium supplemented with 5% (v/v) heat inactivated human AB serum (BioWhittaker) or 10% (v/v) heat inactivated FCS, 2 mM L-glutamine, 100 U/ml penicillin and 100 µg/ml streptomycin (all from Sigma).

Cytokine Detection and Flow Cytometric Analysis

PBMC were resuspended at a concentration of $5 \times 10^6$ cells/ml and added to 96 well round-bottomed plates (250 µl/well). PBMC were incubated with ODN and culture supernatants (SN) were collected after the indicated time points. If not used immediately, SN were stored at −20° C. until required.

Amounts of cytokines in the SN were assessed using an in-house ELISA for IFN-α developed using commercially available antibodies (PBL, New Brunswick, N.J., USA).

Introduction

Oligonucleotides (ODN) containing unmethylated CpG motifs are able to stimulate immune responses through the Toll-like receptor 9 (TLR9) pathway. ODNs with unnatural sugar residues are generally poorer substrates for nucleases as compared to the natural nucleotides. It has been reported that certain types of substitution of 2'-deoxy ribose at the CpG dinucleotide or 5' to the CpG motif results in decreased stimulation of hTLR9 [Zhao et al. (1999) Biorg. Med. Chem. Lett. 9, 3453]; e.g. modification of the 5'-G in GTCpGTT by 2'-O-methyl resulted in strongly decreased activity through the hTLR9 pathway. Surprisingly, FANA-modified ODN do not exhibit the same decrease in hTLR9 activity. The impact of 2'-deoxy-2'-fluoro-β-D-arabino (FANA) nucleosides on the biological activity of CpG ODN is described in the Examples below. FIG. 1 shows that the structures of FANA-modified sugars favor the preferred 2'-endo conformation, unlike the 2'-O-methyl modified sugars which favor the 2'-exo conformation.

Example 1

Oligonucleotides with FANA-Modified G Residues are Stable at Low pH

The mechanism of depurination is shown below:

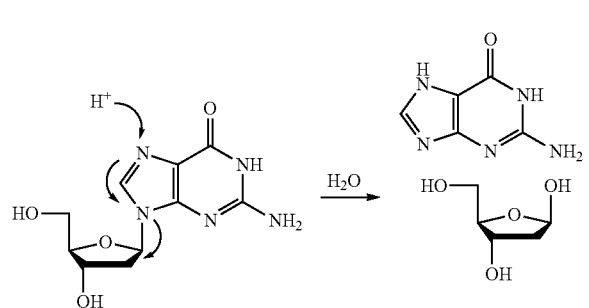

Figure 2:
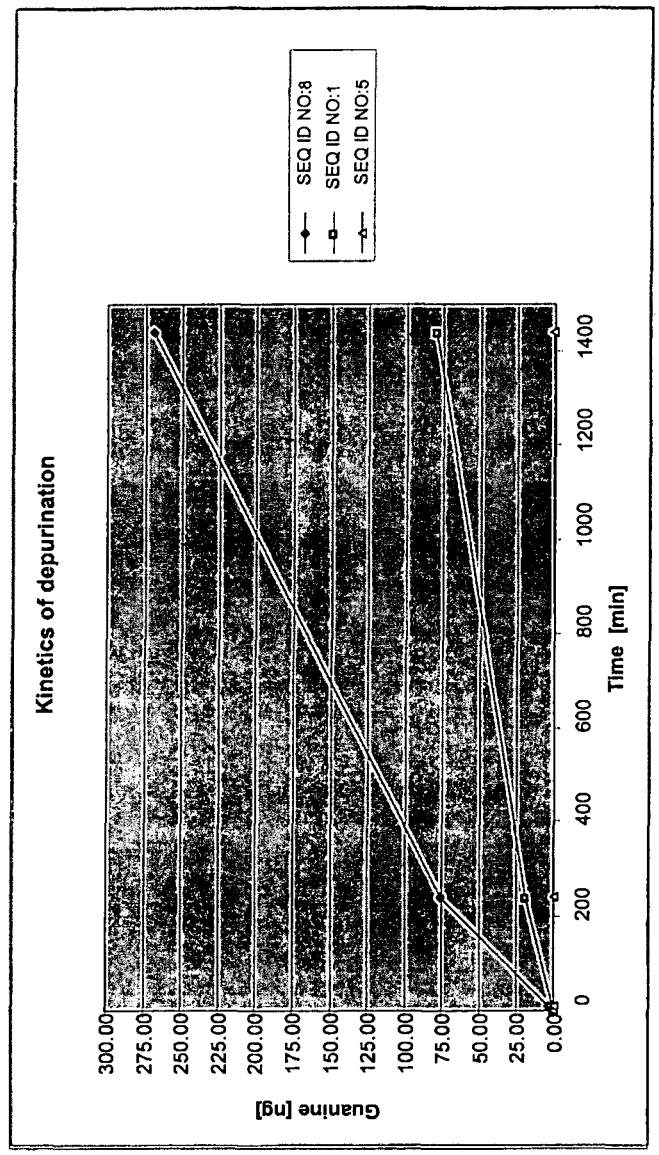
FIG. 2 is a graph showing that nucleic acids with FANA modification of a guanosine residue are stable against acid. Depurination kinetics of FANA nucleic acids SEQ ID NO:1 and SEQ ID NO:5 were compared to the kinetics of the non-FANA parent SEQ ID NO:8. The nucleic acids were incubated in 0.1 M HCl and depurination was measured by RP-HPLC quantification of free purine base. The x-axis is time in minutes and the y-axis is guanine concentration in nanograms (ng).

The stability of SEQ ID NO:1 (one G replaced with faG, see Table 2) and SEQ ID NO:5 (both G's replaced) was investigated. ODN were incubated in 0.1 M HCl, which mimics the pH in the stomach, and depurination was measured over time by RP-HPLC. Acid stability was strongly improved by substitution of G by FANA-modified G (faG) (FIG. 2). SEQ ID NO:5 with all G residues replaced by faG was stable towards acid at pH 1 over the investigated time frame of 24 hours. Even the ODN with only one faG (SEQ ID NO:1) showed increased stability over its unmodified parent sequence (SEQ ID NO:8). This result has significance for the manufacturing of G-rich ODNs, since formation of depurination side products is an issue during acidic removal of the dimethoxytrityl group at the 5'-end of ODNs. More importantly however, ODNs which are stable at pH should be better candidates for oral administration.

Example 2

Figure 3:
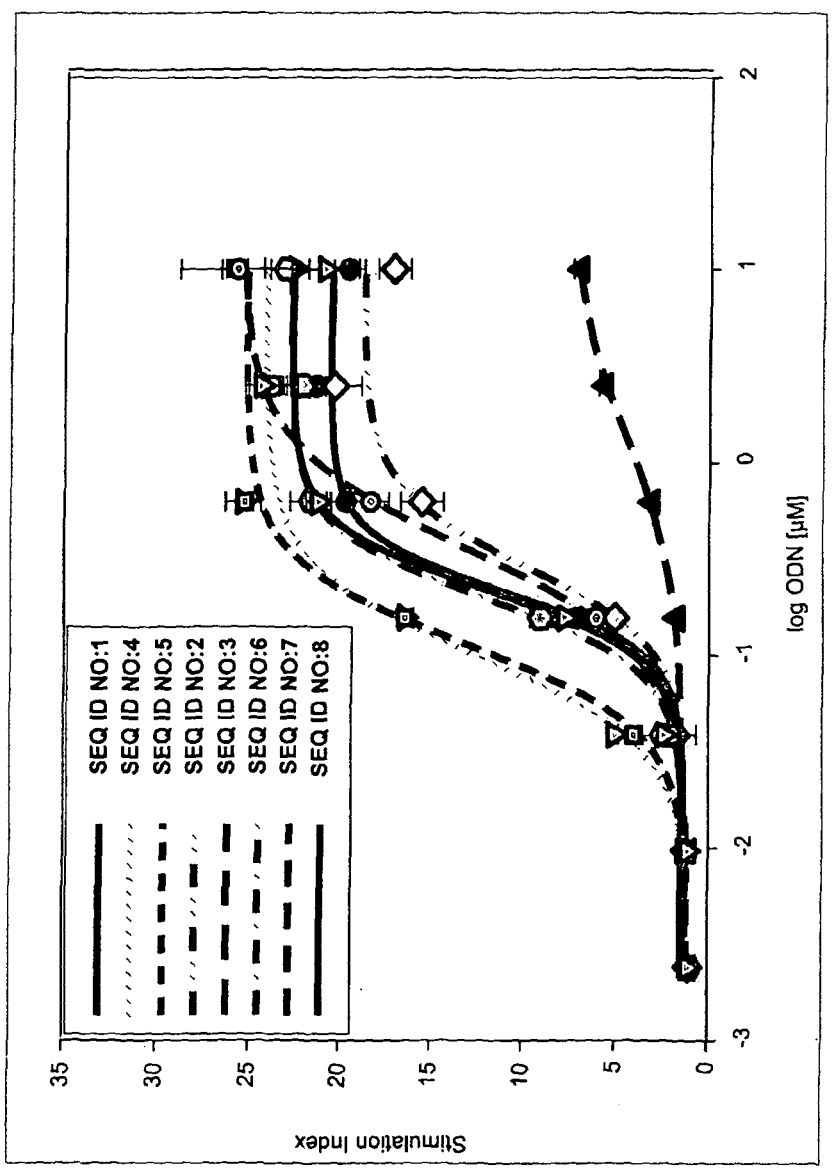
FIG. 3 is a graph showing TLR9-mediated NF-κB activation by B-class FANA nucleic acids. The activities of FANA nucleic acids SEQ ID NO:1-7 were compared to the activity of the non-FANA parent nucleic acid SEQ ID NO:8. hTLR9-LUC-293 cells were incubated with indicated amounts of nucleic acids and NF-κB activation was determined 16 h later by measuring luciferase activity. Stimulation indices were calculated in reference of luciferase activity of medium background. The x-axis is log of ODN concentration in μM and the y-axis is IFN-α concentration in pg/ml.

Incorporation of faG in the CpG Immunostimulatory Motif Leads to an Increase in Human TLR9 Activation in Vitro In order to test the ability of FANA-modified oligonucleotides to activate TLR9, a number of B-class CpG ODN were synthesized with FANA modifications and tested for the ability to activate TLR9. ODNs were incubated with hPBMCs and IFN-α secretion was measured by ELISA. A number of modifications were introduced into the hexamer motif GTCGTT. As shown in FIG. 3, substitution of C by faC (FANA cytidine derivative) at the CpG motif (SEQ ID NO:3) resulted in a strong decrease in hTLR activity as both potency and efficacy were reduced. Surprisingly, substitution of G by faG in the CpG dinucleotide motif (SEQ ID NO:4) resulted in significantly enhanced potency over the faC-modified oligonucleotide. ODN with a substitution of a FANA nucleotide for a T or G in the hexanucleotide motif outside of the CG dinucleotide had similar efficacy and potency as unmodified parent SEQ ID NO:8). When both G nucleotides in the hexanucleotide motif were exchanged for faG (SEQ ID NO:5), efficacy in hTLR9 was significantly better than for the parent ODN.

The improved activity of the ODNs with G replaced by faG is a surprising example in which a modification of the deoxyribose sugar moiety resulted in enhanced activity in hTLR9 assay, rather than the decrease seen with other types of modifications.

TABLE 2

FANA-modified B-class ODN

| Seq ID No: | Sequence |
|---|---|
| 1 | T*faG\*T\*C-G\*T\*T\*T\*T\*T\*T\*T\*T\*T\*T\*T\*T\*T\*T\*T |
| 2 | T\*G\*faT\*C-G\*T\*T\*T\*T\*T\*T\*T\*T\*T\*T\*T\*T\*T\*T\*T |
| 3 | T\*G\*T\*faC-G\*T\*T\*T\*T\*T\*T\*T\*T\*T\*T\*T\*T\*T\*T\*T |
| 4 | T\*G\*T\*C-faG\*T\*T\*T\*T\*T\*T\*T\*T\*T\*T\*T\*T\*T\*T\*T |
| 5 | T\*faG\*T\*C-faG\*T\*T\*T\*T\*T\*T\*T\*T\*T\*T\*T\*T\*T\*T\*T |
| 6 | T\*G\*T\*C-G\*faT\*T\*T\*T\*T\*T\*T\*T\*T\*T\*T\*T\*T\*T\*T |
| 7 | T\*G\*T\*C-G\*T\*faT\*T\*T\*T\*T\*T\*T\*T\*T\*T\*T\*T\*T\*T |
| 8 | T\*G\*T\*C-G\*T\*T\*T\*T\*T\*T\*T\*T\*T\*T\*T\*T\*T\*T\*T | faN = FANA modified nucleotide

Example 3

Incorporation of faG in the CpG Motif Leads to a Slight Increase in IFN-α Secretion In Vitro In order to study the impact of FANA substitution on the capability to induce IFN-α secretion in vitro, C-Class derived ODNs were incubated with hPBMCs and IFN-α secretion was measured by ELISA (see Table 3 and FIG. 4). Surprisingly, SEQ ID NO:9 with the first G at the 5'-end replaced by faG was more potent for inducing IFN-α than the unmodified parent SEQ ID NO:15. Furthermore, substitution of G by faG in C-Class ODN appeared to be generally well tolerated even if all G residues were exchanged.

TABLE 3

FANA-modified C-class ODN

| Seq ID No: | Sequence |
|---|---|
| 9  | T*C*faG*T*C*G*T*T*T*T*C*G*G*C*G*C*G*C*G*C*C*G |
| 10 | T*C*G*T*C*faG*T*T*T*T*C*G*G*C*G*C*G*C*G*C*C*G |
| 11 | T*C*faG*T*C*faG*T*T*T*T*C*G*G*C*G*C*G*C*G*C*C*G |
| 12 | T*C*G*T*C*G*T*T*T*T*C*faG*faG*C*faG*C*faG*C*faG*C*C*G |
| 13 | T*C*faG*T*C*faG*T*T*T*T*C*faG*faG*C*faG*C*faG*C*faG*C*C*G |
| 14 | T*C*faG*T*C*faG*T*T*T*T*C*faG*faG*C*faG*C*faG*C*faG*C*C*3mG |
| 15 | T*C*G*T*C*G*T*T*T*T*C*G*G*C*G*C*G*C*G*C*C*G |
| 16 | T*C*G*T*C*G*T*T*T*T*C*G*G*C*G*C*G*C*G*C*C*3mG | faN = FANA modified nucleotide

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

---

What is claimed is:

1. An immunomodulatory oligonucleotide 8-200 nucleotides in length, comprising at least one immunomodulatory GNCG motif, wherein N is T, A, or a 5-substituted U; and wherein at least one G comprises a 2'-deoxy-2'fluoro-β-D-arabinose (FANA)-modified purine nucleoside.

2. The immunomodulatory oligonucleotide of claim 1, wherein the immunomodulatory motif is GNCG $N_1N_2N_3N_4$.

3. The immunomodulatory oligonucleotide of claim 1, wherein the immunomodulatory motif is a GNCG motif, wherein CG is an internal pyrimidine-guanine dinucleotide.

4. The immunomodulatory oligonucleotide of claim 2, wherein N, $N_1$, $N_2$, $N_3$ and $N_4$ is T.

5. The immunomodulatory oligonucleotide of claim 1, wherein the oligonucleotide includes at least 4 nucleotides 5' to the immunomodulatory motif.

6. The immunomodulatory oligonucleotide of claim 1, wherein at least one nucleotide outside of the immunomodulatory motif has a 2'-deoxy-2'fluoro-β-D-arabinose (FANA) modification.

7. The immunomodulatory oligonucleotide of claim 1, wherein the oligonucleotide comprises a plurality of internal CG dinucleotides and wherein G of every internal CG dinucleotide comprises a 2'-deoxy-2"fluoro-β-D-arabinose (FANA)-modification.

8. The immunomodulatory oligonucleotide of claim 1 wherein the C of the CG dinucleotide is unmethylated.

9. The immunomodulatory oligonucleotide of claim 1, further comprising at least one stabilized internucleotide linkage selected from the group consisting of: phosphorothioate, phosphorodithioate, methylphosphonate, methylphosphorothioate, phosphonoacetate, Rp-phosphorothioate, Sp-phosphorothioate, boranophosphate, or 3'-thioformacetal.

10. The immunomodulatory oligonucleotide of claim 1, further comprising a second type of sugar modification, wherein the second type of sugar modification is selected from the group consisting of 2'-O-methylribose, 2'-O-propanylribose, 2'-O-butylribose, 2'-O-(2-methoxyethyl), 2'-O,4'-C-alkylene-linked ribose (alkylene is methylene (LNA) or ethylene), 2'-deoxy-2'-fluororibose, 3'-O-methyl ribose, 1',2'-dideoxyribose; arabinose, 1'-methylarabinose, 3'-hydroxymethylarabinose, hydroxymethyl-arabinose, or 1,5-anhydrohexitol.

11. The immunomodulatory oligonucleotide of claim 1, further comprising at least one internucleotide linkage and/or at least one internucleotide linkage and/or at least one 2'-5' internucleotide linkage.

12. The immunomodulatory oligonucleotide of claim 1, further comprising at least one palindromic sequence.

13. The immunomodulatory oligonucleotide of claim 1, further comprising at least one $(G)_n$ sequence wherein n is 4 to 10.

14. The immunomodulatory oligonucleotide of claim 1, wherein the oligonucleotide comprises at least one hydrophobic T analog and/or at least one 5-substituted U analog.

15. The immunostimulatory oligonucleotide of claim 1, further comprising a lipophilic modification of the oligonucleotide.

16. The immunomodulatory oligonucleotide of claim 1, wherein the oligonucleotide includes a linker.

17. The immunostimulatory of claim 1, wherein the oligonucleotide sequence is selected from the group consisting of a set comprising SEQ ID NO:1, SEQ ID NO:4, SEQ ID NO:5, SEQ ID NO:9, SEQ ID NO:10, SEQ ID NO:11, SEQ ID NO:13, and to SEQ ID NO:14.

* * * * *